US011147802B2

(12) United States Patent
Wang et al.

(10) Patent No.: US 11,147,802 B2
(45) Date of Patent: Oct. 19, 2021

(54) SUBSTITUTED OXADIAZOLE CHEMICAL COMPOUND AND COMPOSITION CONTAINING SAID CHEMICAL COMPOUND AND USE THEREOF

(71) Applicant: Shenzhen TargetRx, Inc., Shenzhen (CN)

(72) Inventors: Yihan Wang, Shenzhen (CN); Huanyin Li, Shenzhen (CN)

(73) Assignee: Shenzhen TargetRx, Inc., Guangdong (CN)

( * ) Notice: Subject to any disclaimer, the term of this patent is extended or adjusted under 35 U.S.C. 154(b) by 588 days.

(21) Appl. No.: 16/078,551

(22) PCT Filed: Jan. 5, 2017

(86) PCT No.: PCT/CN2017/070279
§ 371 (c)(1),
(2) Date: Aug. 21, 2018

(87) PCT Pub. No.: WO2017/143874
PCT Pub. Date: Aug. 31, 2017

(65) Prior Publication Data
US 2021/0186933 A1  Jun. 24, 2021

(30) Foreign Application Priority Data
Feb. 25, 2016  (CN) .......................... 201610115463.1

(51) Int. Cl.
A61K 31/4245 (2006.01)
C07D 285/01 (2006.01)
A61P 35/00 (2006.01)
A61K 45/06 (2006.01)
C07D 271/08 (2006.01)

(52) U.S. Cl.
CPC .......... A61K 31/4245 (2013.01); A61K 45/06 (2013.01); A61P 35/00 (2018.01); C07D 271/08 (2013.01); C07B 2200/05 (2013.01); C07B 2200/13 (2013.01)

(58) Field of Classification Search
CPC ....... A61K 31/69; A61K 31/4245; C07F 5/02; C07D 285/01; A61P 35/00
USPC .......................... 514/64, 364; 568/6; 548/125
See application file for complete search history.

(56) References Cited

FOREIGN PATENT DOCUMENTS

| CN | 1835580 A | 9/2006 |
|---|---|---|
| CN | 101047833 A | 10/2007 |
| CN | 101102460 A | 1/2008 |
| CN | 101668170 A | 3/2010 |
| CN | 101932325 A | 12/2010 |
| CN | 102164902 A | 8/2011 |
| JP | H09510717 A | 10/1997 |
| JP | 2010-539166 A | 12/2010 |
| JP | 2011-527686 A | 11/2011 |
| WO | WO 2010/005958 A2 | 1/2010 |
| WO | WO 2010/028015 A2 | 3/2010 |
| WO | WO 2014/066834 A1 | 5/2014 |
| WO | WO 2015/119944 A1 | 8/2015 |

OTHER PUBLICATIONS

PCT/CN2017/070279, Mar. 29, 2017, International Search Report and Written Opinion (with English translation).
PCT/CN2017/070279, Sep. 7, 2018, International Preliminary Report on Patentability.
EP 17755703.0, Oct. 30, 2018, Extended European Search Report.
Foster. Deuterium Isotope Effects in the Metabolism of Drugs and Xenobiotics: Implications for Drug Design. In: Advances in Drug Research. 1985. Testa Ed. vol. 14:1-40. ISBN 0-12-013314-8.
Jiang et al., Application of deuteration in drug research. Qilu Pharmaceutical Affaris. Dec. 2010;29(11):682-4.
Buteau, Deuterated Drugs: Unexpectedly Nonobvious? J. High Tech. Law. 2009;10(1):22-74.
O'Driscoll, Heavyweight drugs. Chemistry and Industry. Mar. 9, 2009:24-6.

Primary Examiner — Raymond J Henley, III
(74) Attorney, Agent, or Firm — Wolf, Greenfield & Sacks, P.C.

(57) ABSTRACT

Provided are a substituted oxadiazole chemical compound and composition containing said chemical compound and use thereof; said substituted oxadiazole chemical compound is the oxadiazole chemical compound as represented by formula (I), or its crystalline form, pharmaceutically acceptable salt, prodrug, stereoisomer, hydrate, or solvent compound. The disclosed substituted oxadiazole chemical compound and composition containing said chemical compound are capable of inhibiting indoleamine 2,3-dioxygenase; it also has better pharmacokinetic parameter attributes and is capable of improving the drug concentration of the chemical compound in an animal body, thus improving the therapeutic efficacy and safety of the drug.

Formula (I)

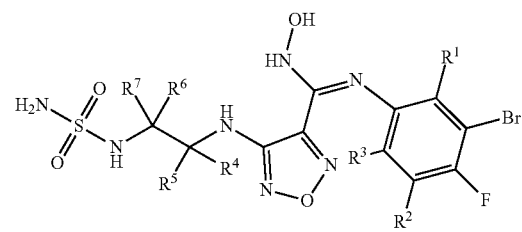

20 Claims, No Drawings

SUBSTITUTED OXADIAZOLE CHEMICAL COMPOUND AND COMPOSITION CONTAINING SAID CHEMICAL COMPOUND AND USE THEREOF

CROSS REFERENCE TO RELATED APPLICATIONS

This application is a national stage filing under 35 U.S.C. 371 of International Patent Application Serial No. PCT/CN2017/070279, filed Jan. 5, 2017, entitled "SUBSTITUTED OXADIAZOLE CHEMICAL COMPOUND AND COMPOSITION CONTAINING SAID CHEMICAL COMPOUND AND USE THEREOF", which claims priority to Chinese patent application number 201610115463.1, filed Feb. 25, 2016, the entire contents of each of which are incorporated by reference herein.

TECHNICAL FIELD

The present disclosure belongs to the pharmaceutical field, and in particular relates to a substituted oxadiazole compound and a composition comprising the same and the use thereof.

BACKGROUND OF THE INVENTION

Indoleamine 2,3-dioxygenase (IDO) is an enzyme that contains heme in cells. It is the only rate-limiting enzyme outside the liver that can catalyze the metabolism of tryptophan to degrade via a kynurenine pathway to a series of metabolites including quinolinic acid (C. MacKenzie, et. al., Current Drug Metabolism, 2007, 3, 237-244).

Inhibitors of Indoleamine 2,3-dioxygenase (IDO) can treat tumors. Studies have shown that the currently recognized IDO inhibitor 1-methyltryptophan (1-MT) can enhance the sensitivity of tumor cells to T-cell immunostimulation in vitro, and can delay tumor cell growth, enhance antitumor effects of chemotherapeutic agents and acts on almost all of spontaneous tumors in animal models in vivo (M. Friberg et. al., Int J Cancer, 2002, 101, 151-155). IDO inhibitors can treat mood disorders and other diseases with pathological features of the IDO-mediated tryptophan metabolism pathway, including: AIDS, neurodegenerative diseases (Alzheimer's disease, Huntington's disease, and Parkinson's disease), depression, cataracts, age-related macular degeneration, and autoimmune diseases.

Although IDO was cloned as early as in the 1960s, it was not found until recently that IDO was also very important for the regulation of the immune system. The high expression of IDO leads to the depletion of tryptophan locally in the cells and induces T-cells arrest at G1 phase, thereby inhibiting the proliferation of T-cells. On the other hand, IDO-dependent tryptophan degradation leads to an increased kynurenine level and also induces oxygen free radical-mediated T-cells apoptosis. Third, up-regulation of IDO expression in dendritic cells enhances local regulatory T-cells (Treg)-mediated immunosuppression by degrading local tryptophan, prompting body's peripheral immune tolerance to tumor-specific antigens.

However, no IDO inhibitors are marketed yet. Incyte's Epacadostat is an oral, potent, and selective small-molecule IDO inhibitor, and the development thereof is currently under Phase 2 clinical stage. Therefore, it is a urgent need to develop more effective IDO inhibitors.

SUMMARY OF THE INVENTION

In view of the above technical problems, the present disclosure discloses a substituted oxadiazole compound, a composition comprising the same, and the use thereof, which have better inhibitory activity against indoleamine 2,3-dioxygenase and/or better pharmacodynamic/pharmacokinetic properties, and thus can be used to treat, prevent, and alleviate diseases mediated by indoleamine 2,3-dioxygenase.

In this regard, the technical solution disclosed herein is:

A substituted oxadiazole compound, as shown by the oxadiazole compound represented by formula (I), or a crystal form, pharmaceutically acceptable salt, hydrate or solvate thereof, Formula (1)

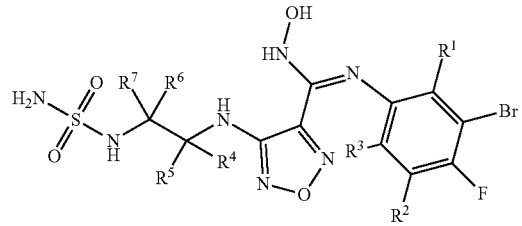

wherein $R^1$, $R^2$, $R^3$, $R^4$, $R^5$, $R^6$, and $R^7$ are each independently hydrogen, deuterium, or halogen;

provided that at least one of $R^1$, $R^2$, $R^3$, $R^4$, $R^5$, $R^6$ and $R^7$ is deuterated or deuterium.

As a further embodiment disclosed herein, $R^1$, $R^2$, and $R^3$ are each independently deuterium or hydrogen.

As a further embodiment disclosed herein, $R^4$ and $R^5$ are each independently deuterium or hydrogen.

As a further embodiment disclosed herein, $R^6$ and $R^7$ are each independently deuterium or hydrogen.

In another embodiment, the compound disclosed herein may be selected from, but not limited to, the following group of compounds or pharmaceutically acceptable salts thereof:

Formula (2)

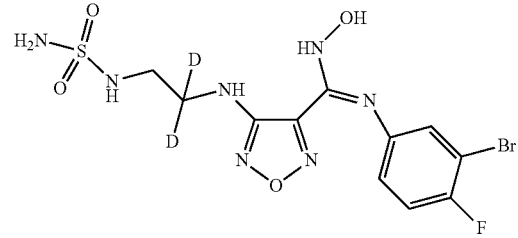

Formula (3)

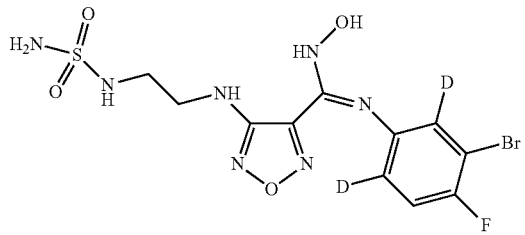

Formula (4)
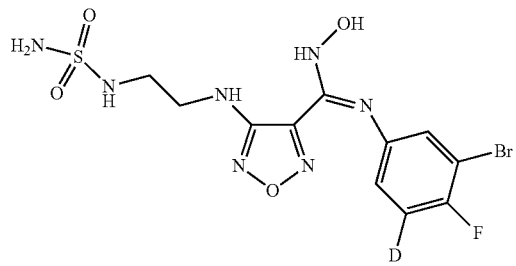
Formula (5)
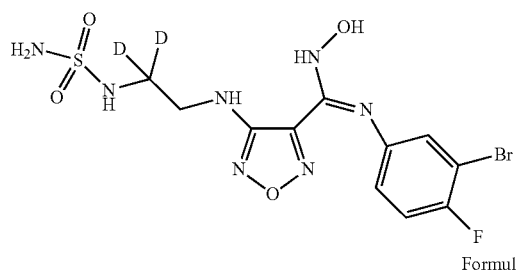
Formula (6)
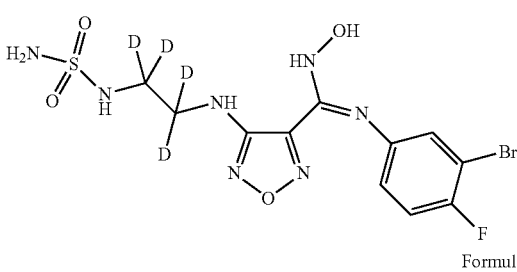
Formula (7)
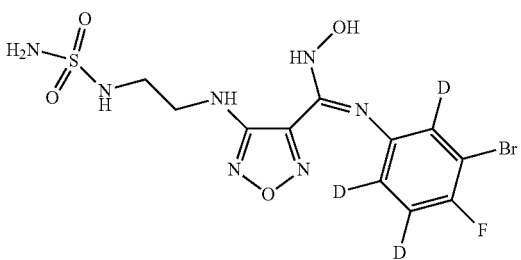
Formula (8)
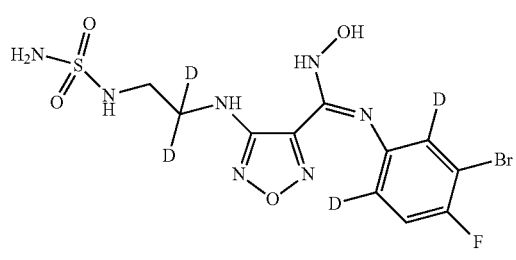
Formula (9)
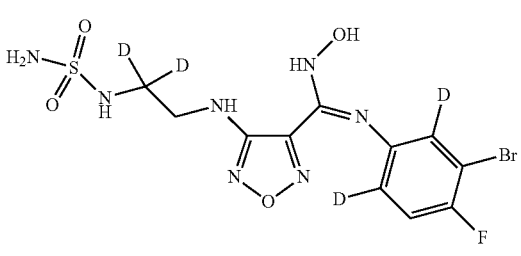
Formula (10)
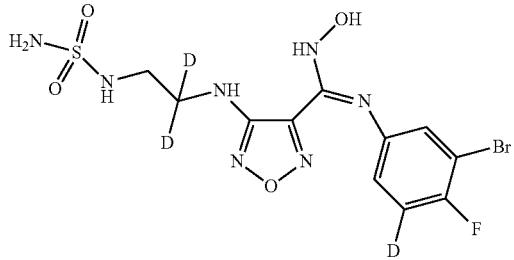
Formula (11)
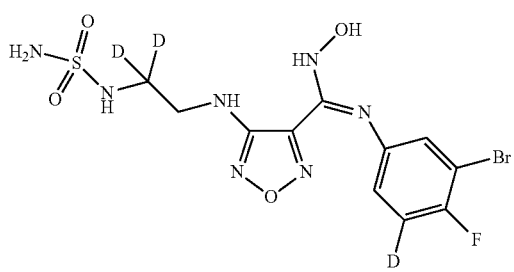
Formula (12)
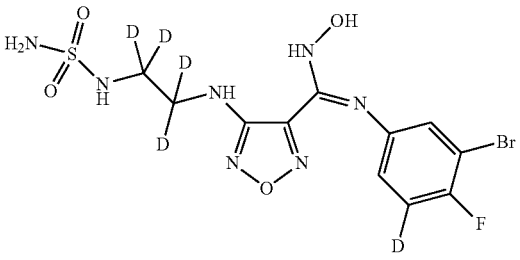
Formula (13)
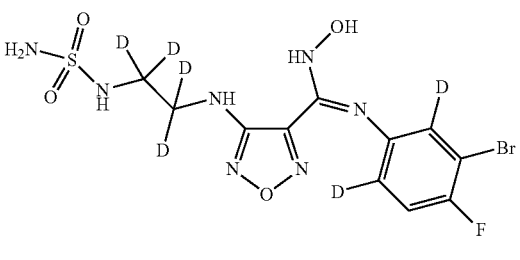
Formula (14)
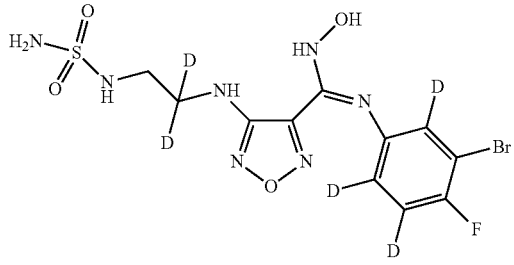

Formula (15)
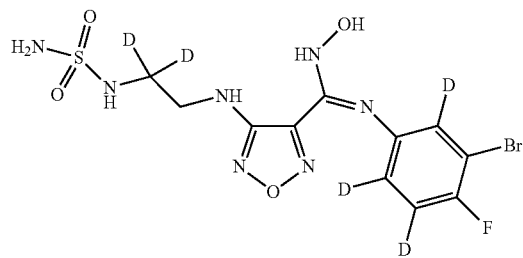

Formula (16)
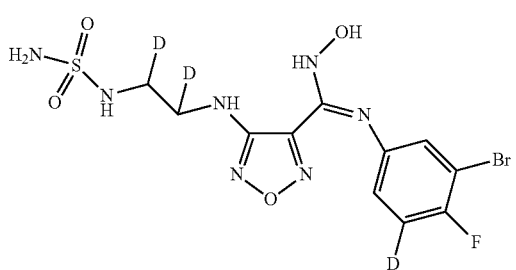

Formula (17)
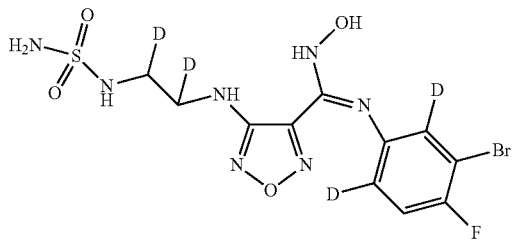

Formula (18)
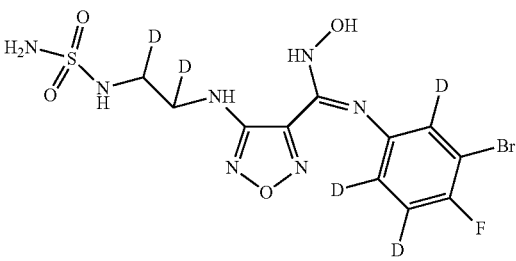

Formula (19)
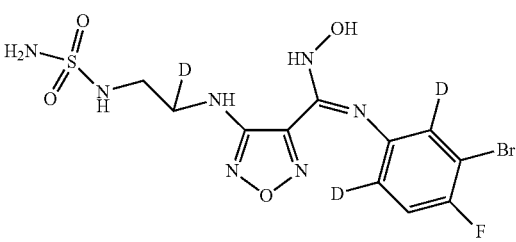

Formula (20)
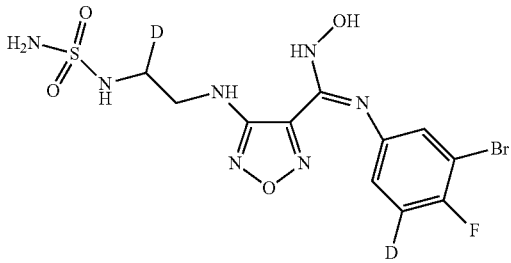

Formula (21)
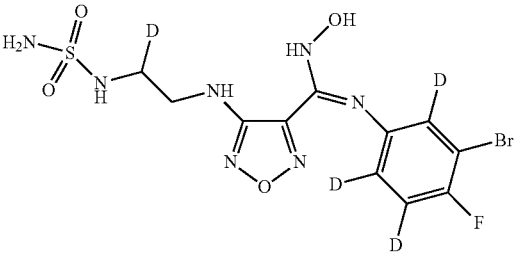

Formula (22)
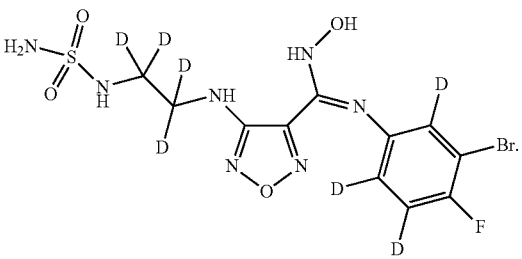

As a further embodiment disclosed herein, the content of the deuterium isotope at the deuterated position is at least greater than the natural content of the deuterium isotope (0.015%), preferably greater than 30%, more preferably greater than 50%, still more preferably greater than 75%, still more preferably greater than 95%, and still more preferably greater than 99%.

In another embodiment, the content of the deuterium isotope in each deuterated position is at least greater than the natural content of the deuterium isotope (0.015%), preferably greater than 30%, more preferably greater than 50%, still more preferably greater than 75%, still more preferably greater than 95%, and still more preferably greater than 99%.

Specifically, in the present disclosure, the content of the deuterium isotope in each deuterated position of $R^1$, $R^2$, $R^3$, $R^4$, $R^5$, $R^6$ and $R^7$ is at least 5%, preferably greater than 10%, more preferably greater than 15%, more preferably greater than 20%, still more preferably greater than 25%, still more preferably greater than 30%, still more preferably greater than 35%, still more preferably greater than 40%, still more preferably greater than 45%, still more preferably greater than 50%, still more preferably greater than 55%, still more preferably greater than 60%, still more preferably greater than 65%, still more preferably greater than 70%, still more preferably greater than 75%, more preferably greater than 80%, still more preferably greater than 85%, still more preferably greater than 90%, still more preferably greater than 95%, and still more preferably greater than 99%.

In another embodiment, in $R^1$, $R^2$, $R^3$, $R^4$, $R^5$, $R^6$, and $R^7$ of the compound of Formula (I), at least one R contains deuterium, and more preferably two Rs, more preferably three Rs, more preferably four Rs, more preferably five Rs, more preferably six Rs, more preferably seven Rs contain deuterium.

As a further embodiment disclosed herein, a pharmaceutically acceptable carrier and a substituted oxadiazole compound as described above, or a crystal form, pharmaceutically acceptable salt, prodrug, stereoisomer, isotopic variant, hydrate or solvate thereof are mixed to form a pharmaceutical composition.

Also disclosed herein is a pharmaceutical composition comprising a pharmaceutically acceptable carrier and a substituted oxadiazole compound as described above, or a crystal form, pharmaceutically acceptable salt, hydrate or solvate, stereoisomer, prodrug, or isotopic variant thereof.

Also included is isotopically labeled compounds to the extent of the original compounds disclosed herein. Examples of isotopes that can be used in compounds disclosed herein include hydrogen, carbon, nitrogen, oxygen, phosphorus, sulfur, fluorine, and chlorine isotopes, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds disclosed herein, or enantiomers, diastereomers, isomers, or pharmaceutically acceptable salts or solvates thereof, in which the isotopes as described above or other isotope atoms are contained, are within the scope of the present disclosure. Certain isotopically labeled compounds disclosed herein, such as the radioisotopes of $^3$H and $^{14}$C, are also among them and are useful in the tissue distribution experiments of drugs and substrates. Tritium, i.e., $^3$H, and carbon-14, i.e., $^{14}$C, are easier to prepare and detect and are the first choice for isotopes. Isotopically-labeled compounds can be prepared using the schemes shown in the Examples by conventional methods by replacing the non-isotopic reagents with readily available isotopically labeled reagents.

As a further embodiment disclosed herein, it further comprises other therapeutic drugs, which are drugs for treating cancer, cell proliferative diseases, inflammation, infections, immune diseases, organ transplantation, viral diseases, cardiovascular diseases or metabolic diseases, or antiviral agents.

Suitable antiviral agents for use in combination with the compounds disclosed herein may include nucleoside and nucleotide reverse transcriptase inhibitors (NRTI), non-nucleoside reverse transcriptase inhibitors (NNRTI), protease inhibitors, and other antiviral agents.

Examples of suitable NRTIs include: zidovudine, didanosine, zalcitabine, stavudine, lamivudine, abacavir, adefovir dipivoxil, lobucavir, BCH-10652, emtricitabine, β-L-FD4 (also known as (β-L-D4C) and lodenosine.

Typical and suitable NNRTIs include nevirapine, delavirdine, efavirenz, PNU-142721, AG-1549, MKC-442 (1-(ethoxy-methyl)-5-(1-methylethyl)-6-(phenylmethyl)-(2,4 (1H,3H)-pyrimidinedione) and (+)-calophyllum extract.

Typical and suitable protease inhibitors include saquinavir, ritonavir, indinavir, nelfinavir, amprenavir, lasinavir, DMP-450, BMS-2322623, ABT-378, and AG-1 549.

Other antiviral agents include hydroxyurea, ribavirin, IL-2, IL-12, pentafuside, and Yissum item number 11607.

Suitable chemotherapeutic agents or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, and temozolomide.

In the treatment of melanoma, suitable agents for use in combination with the compounds disclosed herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds disclosed herein may also be combined with immunotherapy drugs, including cytokines such as interferon alpha, interleukin 2, and tumor necrosis factor (TNF) in the treatment of melanoma.

Compounds disclosed herein may also be used in combination with vaccine therapy in the treatment of melanoma. Antimelanoma vaccines are, in some ways, similar to the antivirus vaccines which are used to prevent diseases caused by viruses such as polio, measles, and mumps. Weakened melanoma cells or parts of melanoma cells called antigens may be injected into a patient to stimulate the body's immune system to destroy melanoma cells.

The pharmaceutical composition disclosed herein comprises a compound disclosed herein or a pharmacologically acceptable salt thereof within a safe and effective amount and a pharmacologically acceptable excipient or carrier. The "safe and effective amount" refers to the amount of compound sufficient to significantly improve the condition without causing serious side effects. In general, the pharmaceutical compositions contain 1-2000 mg of the compound/agent disclosed herein, more preferably, 10-1000 mg of the compound/agent disclosed herein. Preferably, the "one dose" is a capsule or tablet.

Also disclosed is use of a substituted oxadiazole compound as described above, or a crystal form, a pharmaceutically acceptable salt, a hydrate or a solvate thereof in the preparation of a pharmaceutical composition for the treatment, prevention, and alleviation of an indoleamine 2,3-dioxygenase-mediated disease.

Since the compound disclosed herein has excellent inhibitory activity against indoleamine 2,3-dioxygenase, the compound disclosed herein and various crystal forms, pharmaceutically acceptable inorganic or organic salts, hydrates or solvates thereof, and the pharmaceutical composition containing the compound disclosed herein as a main active ingredient can be used to treat, prevent and alleviate diseases mediated by indoleamine 2,3-dioxygenase. According to the prior art, the compounds disclosed herein can be used to treat the following diseases: mood disorders and other diseases with pathological features of the IDO-mediated tryptophan metabolism pathway, including: cancer, AIDS, melanoma, neurodegenerative diseases (Alzheimer's disease, Huntington's disease and Parkinson's disease), depression, cataracts, age-related macular degeneration, autoimmune diseases and the like.

The substituted oxadiazole compounds disclosed herein may be combined with immune checkpoint inhibitors.

The immune checkpoint inhibitors are selected from CTLA-4, PD-1, and PD-L1 inhibitors.

The CTLA-4, PD-1, and PD-L1 inhibitors include but are not limited to the following: Nivolumab, Pembrolizumab, Atezolizumab, Durvalumab, and Avelumab.

the beneficial effects of the present disclosure are:
the substituted oxadiazole compounds disclosed herein and compositions comprising the same have excellent inhibitory properties against indoleamine 2,3-dioxygenase and have better pharmacokinetic parameters and can increase the drug concentration of the compound in the animal body to improve the efficacy and safety of the drug; the substituted oxadiazole compound disclosed herein and the composition comprising the same can be used to treat, prevent and relieve the indoleamine 2,3-dioxygenase-mediated diseases.

DETAILED DESCRIPTION

In the following, further detailed descriptions will be given in conjunction with the preferred embodiments of the present disclosure.

It should be understood that these examples are only for illustrating the present disclosure and are not intended to limit the scope of the present disclosure. The experimental methods that do not specify the specific conditions in the following examples are generally based on conventional conditions or according to manufacturer's recommended conditions. Parts and percentages are parts by weight and percentages by weight unless otherwise indicated.

Example 1

Preparation of 4-({2-[sulfamoyl)amino]-1,1-d$_2$-ethyl}amino)-N-(3-bromo-4-fluorophenyl)-N'-hydroxy-1,2,5-oxadiazole-3-carboximidamide (Compound 11)

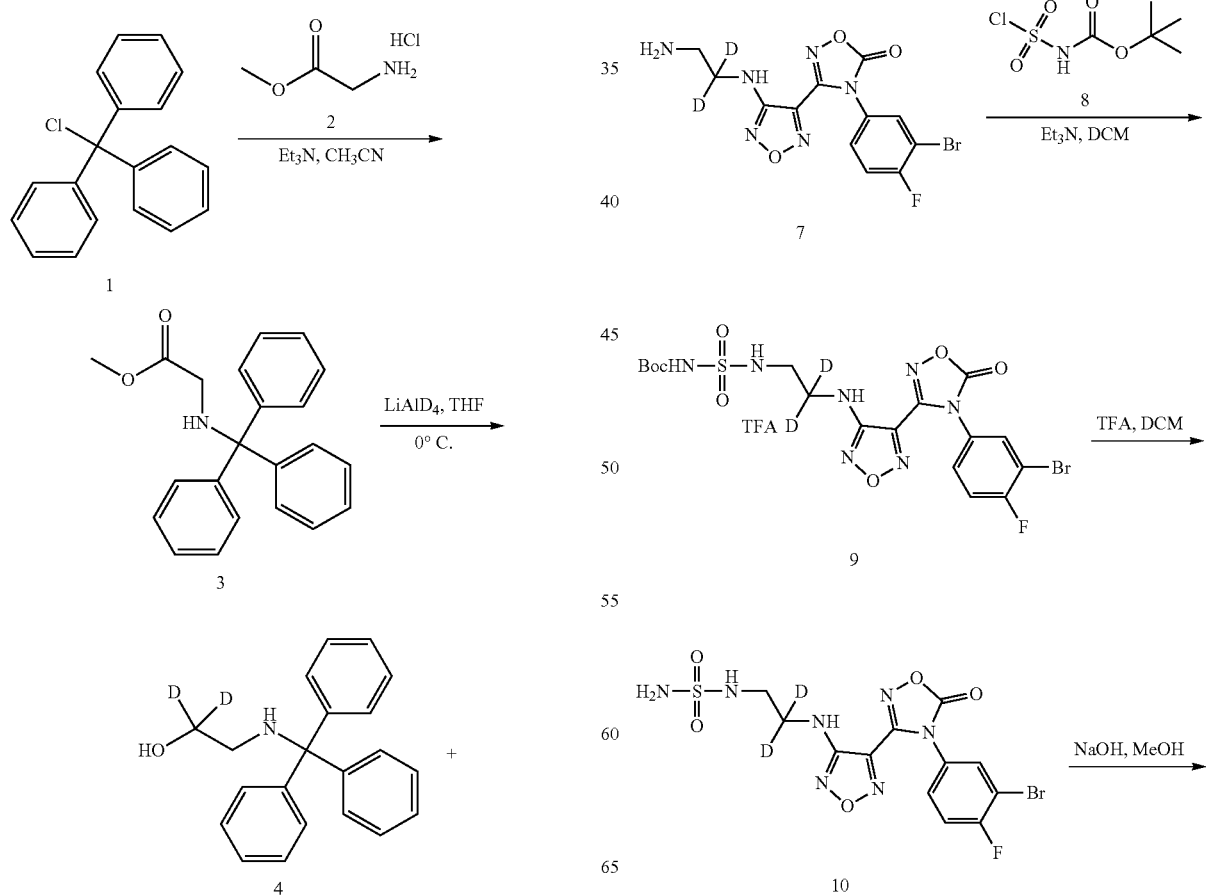

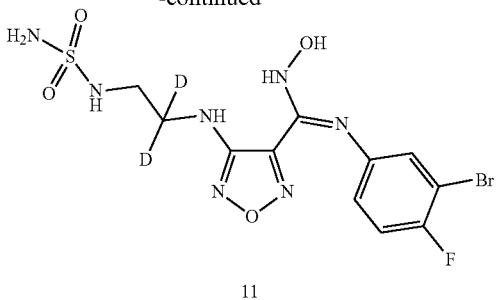

11

Step 1 Synthesis of Compound 3

Triphenylmethyl chloride (2.78 g, 10 mmol) and triethylamine (10 mL, 72 mmol) were added in turn to a solution of methyl 2-aminoacetate hydrochloride (3 mL, 10 mmol) in acetonitrile (15 mL) at 0° C. After stirring at room temperature overnight, the reaction mixture was quenched with water and extracted with dichloromethane. The organic phase was separated and purified by column to obtain 3.2 g of a white solid product. The yield was 44%. LC-MS (APCI): m/z=332.0 (M+1)$^+$.

Step 2 Synthesis of Compound 4

Compound 3 (2 g, 6.6 mmol) and tetrahydrofuran (30 mL) were added to a three-necked flask at 0° C., and LiAlD$_4$ (0.28 g, 6.6 mmol) was slowly poured into the mixture. After stirring at room temperature for 1 hour, sodium sulfate was added until the reaction mixture became a slurry mixture. After filtration, the filtrate was dried on a rotary evaporator and purified to obtain 800 mg of a white solid product. The yield was 40%. LC-MS (APCI): m/z=306.2 (M+1)$^+$, $^1$H NMR (300 MHz, CDCl$_3$) (δ/ppm) 7.49-7.47 (m, 6H), 7.31-7.27 (m, 6H), 7.22-7.18 (m, 3H), 2.35 (s, 2H).

Step 3 Synthesis of Compound 6

To a solution of compound 4 (800 mg, 2.6 mmol) and triphenyl phosphate (914 mg, 2.8 mmol) in tetrahydrofuran (15 mL) was slowly added dropwise diisopropyl azodicarboxylate (566 mg, 2.8 mmol) at 0° C. and stirring was continued. After 15 minutes, a solution of compound 5 (880 mg, 2 mmol) in tetrahydrofuran (5 mL) was added to give a yellow suspension, which was stirred at room temperature overnight and then purified by column to give 261 mg of a white solid product with a yield of 21%. LC-MS (APCI): m/z=629.2 (M+1)$^+$.

Step 4 Synthesis of Compound 7

A mixture of triisopropylsilane (TISiH, 0.13 ml, 0.6 mmol) and trifluoroacetic acid (1.5 ml, 20 mmol) was added to compound 6 (261 mg, 0.4 mmol), stirred at room temperature for 30 minutes, filtered and washed with trifluoroacetic acid. The filtrate was collected to obtain an oil. The oil was dissolved in methanol and cooled to 0° C. 4M solution of HCl in 1,4-dioxane was added, and stirred at room temperature for 15 minutes. The solution was dried on a rotary evaporator, dissolved in diethyl ether, and filtered to give 109 mg of a white solid product with a yield of 65%. LC-MS (APCI): m/z=387.0 (M+1)$^+$.

Step 5 Synthesis of Compound 9

To a solution of chlorosulfonyl isocyanate (73 mg, 0.52 mmol) in dichloromethane (5 mL) was added dropwise tert-butanol (39 mg, 0.52 mmol) at 0° C. The mixture was stirred at room temperature for 1 hour and added to a suspension of compound 7 (109 mg, 0.26 mmol) in dichloromethane (5 mL), and triethylamine (0.15 mL) were added at 0° C. Stirring was continued for 3 hours at room temperature. After dilution with 0.1 N hydrochloric acid, the mixture was extracted with ethyl acetate and the organic phase was collected to give the product as a white solid which was used directly in the next step. LC-MS (APCI): m/z=566.0 (M+1)$^+$.

Step 6 Synthesis of Compound 10

Compound 9 was dissolved in dichloromethane (5 mL), 1 mL of trifluoroacetic acid was added, and then the mixture was stirred at room temperature for 2 hours. The organic phase was collected and used directly in the next step. LC-MS (APCI): m/z=466.1 (M+1)$^+$.

Step 7 Synthesis of Compound 11

A 2M sodium hydroxide solution (1.2 mL, 2.4 mmol) was added to a solution of compound 10 in methanol (5 mL). After stirring at room temperature for 2 hours, a 6N hydrochloric acid solution was added to adjust the pH to neutral. The methanol was removed. The residue was diluted with water (10 mL) and extracted with ethyl acetate. The organic phase was collected and purified by column to give 39 mg of a yellow solid. LC-MS (APCI): m/z=440.0 (M+1)$^+$; $^1$H NMR (300 MHz, DMSO-d$_6$) (δ/ppm) 11.50 (s, 1H), 8.89 (s, 1H), 7.17 (t, J=9.0 Hz, 1H), 7.12-7.09 (m, 1H), 6.79-6.75 (m, 1H), 6.71-6.68 (m, 1H), 6.58 (s, 2H), 6.24-6.21 (m, 1H), 3.34 (d, J=6.0 Hz, 1H), 3.08 (t, J=6.0 Hz, 2H).

Example 2

Preparation of 4-({2-[sulfamoyl)amino]ethyl}amino)-N-(2,6-d$_2$-3-bromo-4-fluorophenyl)-N'-hydroxy-1,2,5-oxadiazole-3-carboximidamide (Compound 22)

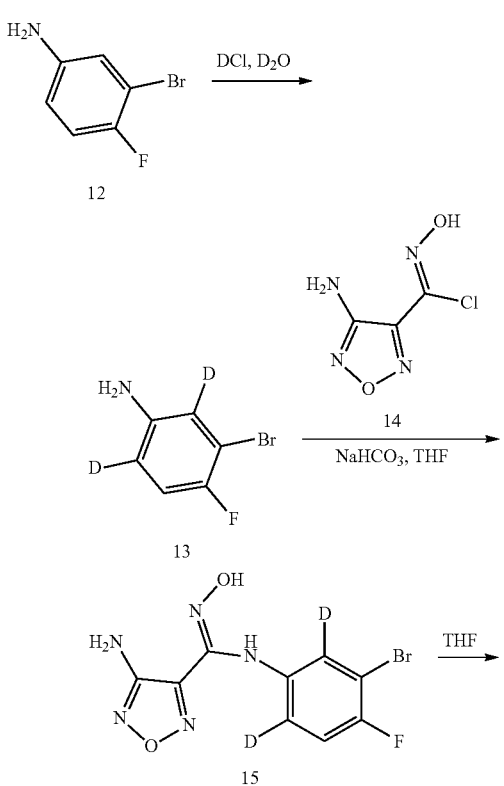

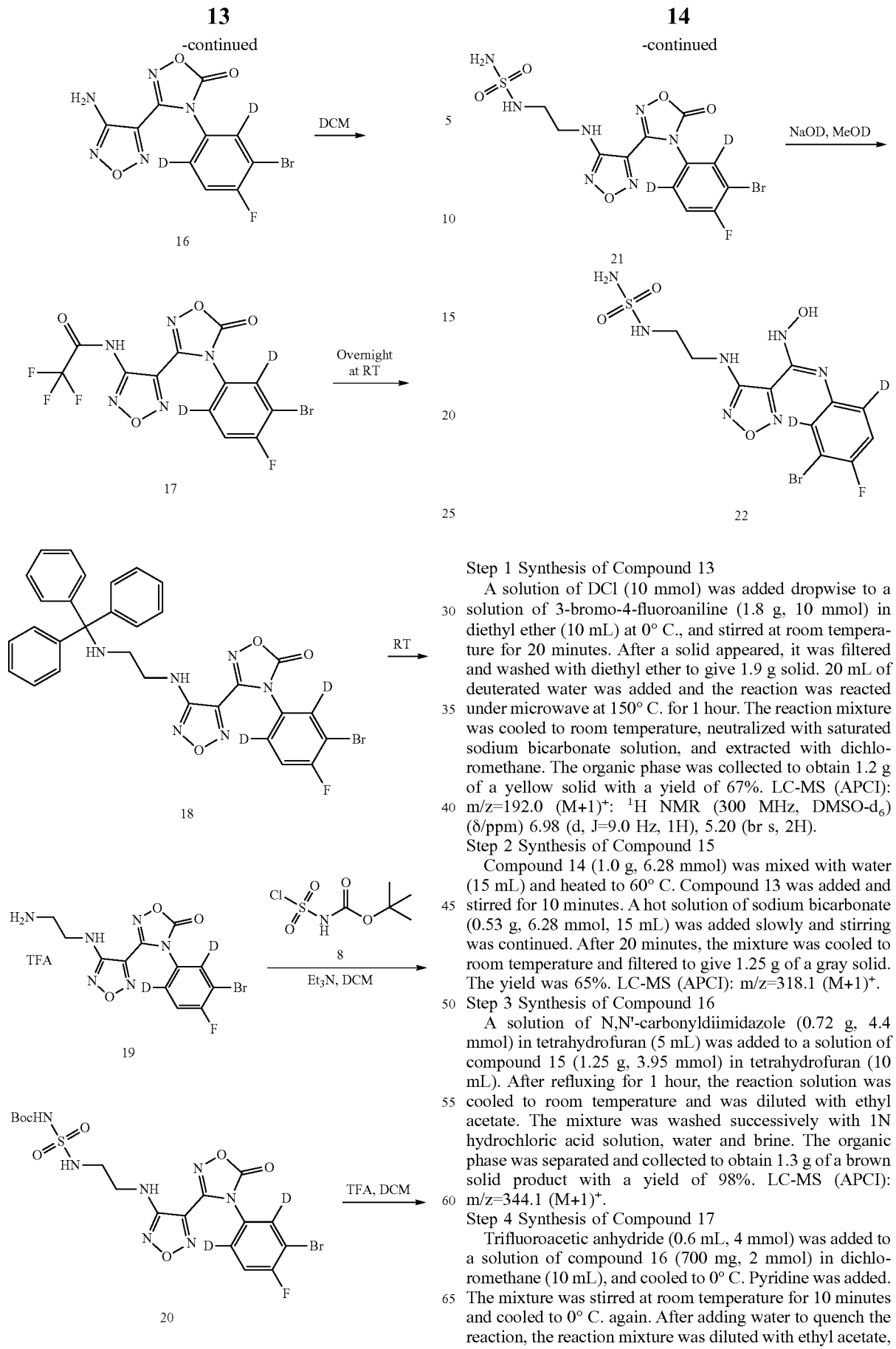

Step 1 Synthesis of Compound 13

A solution of DCl (10 mmol) was added dropwise to a solution of 3-bromo-4-fluoroaniline (1.8 g, 10 mmol) in diethyl ether (10 mL) at 0° C., and stirred at room temperature for 20 minutes. After a solid appeared, it was filtered and washed with diethyl ether to give 1.9 g solid. 20 mL of deuterated water was added and the reaction was reacted under microwave at 150° C. for 1 hour. The reaction mixture was cooled to room temperature, neutralized with saturated sodium bicarbonate solution, and extracted with dichloromethane. The organic phase was collected to obtain 1.2 g of a yellow solid with a yield of 67%. LC-MS (APCI): m/z=192.0 (M+1)$^+$: $^1$H NMR (300 MHz, DMSO-$d_6$) (δ/ppm) 6.98 (d, J=9.0 Hz, 1H), 5.20 (br s, 2H).

Step 2 Synthesis of Compound 15

Compound 14 (1.0 g, 6.28 mmol) was mixed with water (15 mL) and heated to 60° C. Compound 13 was added and stirred for 10 minutes. A hot solution of sodium bicarbonate (0.53 g, 6.28 mmol, 15 mL) was added slowly and stirring was continued. After 20 minutes, the mixture was cooled to room temperature and filtered to give 1.25 g of a gray solid. The yield was 65%. LC-MS (APCI): m/z=318.1 (M+1)$^+$.

Step 3 Synthesis of Compound 16

A solution of N,N'-carbonyldiimidazole (0.72 g, 4.4 mmol) in tetrahydrofuran (5 mL) was added to a solution of compound 15 (1.25 g, 3.95 mmol) in tetrahydrofuran (10 mL). After refluxing for 1 hour, the reaction solution was cooled to room temperature and was diluted with ethyl acetate. The mixture was washed successively with 1N hydrochloric acid solution, water and brine. The organic phase was separated and collected to obtain 1.3 g of a brown solid product with a yield of 98%. LC-MS (APCI): m/z=344.1 (M+1)$^+$.

Step 4 Synthesis of Compound 17

Trifluoroacetic anhydride (0.6 mL, 4 mmol) was added to a solution of compound 16 (700 mg, 2 mmol) in dichloromethane (10 mL), and cooled to 0° C. Pyridine was added. The mixture was stirred at room temperature for 10 minutes and cooled to 0° C. again. After adding water to quench the reaction, the reaction mixture was diluted with ethyl acetate, and washed sequentially with 1N hydrochloric acid solution, water, and brine. The organic phase was collected to obtain 996 mg of a brown solid product with a yield of 98%. LC-MS (APCI): m/z=440.1 (M+1)+.

Step 5 Synthesis of Compound 18

To a solution of 2-(triphenylamino)ethanol (5000 mg, 1.5 mmol) and triphenyl phosphate (502 mg, 1.54 mmol) in tetrahydrofuran (10 mL) was slowly added dropwise diisopropyl azodicarboxylate at 0° C. After stirring for 15 minutes, a solution of compound 17 (331 mg, 1.54 mmol) in tetrahydrofuran (5 mL) was added to give a yellow suspension which was stirred overnight at room temperature and purified by column to give a white solid product (240 mg) with a yield of 35%. LC-MS (APCI): m/z=192.0 (M+1)+; $^1$H NMR (300 MHz, DMSO-$d_6$) (δ/ppm) 11.49 (s, 1H), 8.88 (s, 1H), 7.17 (d, J=8.8 Hz, 1H), 6.71 (t, J=6.0 Hz, 1H), 6.59 (s, 2H), 6.24 (t, J=6.0 Hz, 1H), 3.37 (q, J=6.0 Hz, 2H), 3.11 (q, J=6.0 Hz, 2H).

Step 6 Synthesis of Compound 19

The reaction procedure was the same as that of Example 1, Step 4, and the resulting oily product was used directly in the next step. LC-MS (APCI): m/z=387.0 (M+1)+.

Step 7 Synthesis of Compound 20

The reaction procedure was the same as that of Example 1, Step 5, and the resulting white solid product was used directly in the next step. LC-MS (APCI): m/z=566.1 (M+1)+.

Step 8 Synthesis of Compound 21

The reaction procedure was the same as that of Example 1, Step 6, and the resulting white solid product was used directly in the next step. LC-MS (APCI): m/z=466.1 (M+1)+.

Step 9 Synthesis of Compound 22

The reaction procedure was the same as that of Example 1, Step 7, and 55 mg of a yellow solid product was obtained. LC-MS (APCI): m/z=440.1 (M+1)+; $^1$H NMR (400 MHz, DMSO-$d_6$) (δ/ppm) 11.49 (s, 1H), 8.88 (s, 1H), 7.17 (d, J=8.8 Hz, 1H), 6.71 (t, J=6.0 Hz, 1H), 6.59 (s, 2H), 6.24 (t, J=6.0 Hz, 1H), 3.37 (q, J=6.0 Hz, 2H), 3.11 (q, J=6.0 Hz, 2H).

Example 3

Preparation of 4-({2-[(sulfamoyl)amino]ethyl}amino)-N-(3-bromo-4-fluoro-5-d-phenyl)-N'-hydroxy-1,2,5-oxadiazole-3-carboximidamide (Compound 32)

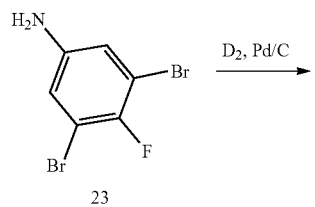

23

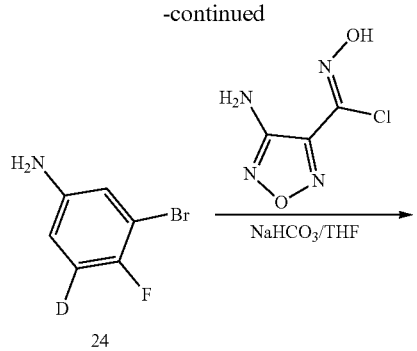

24

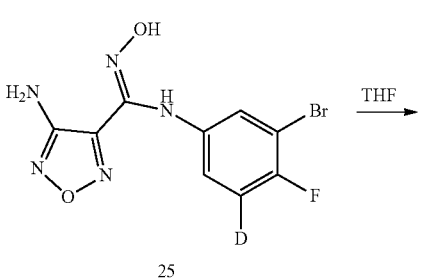

25

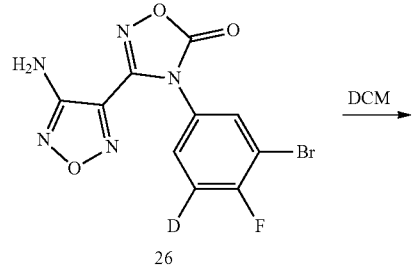

26

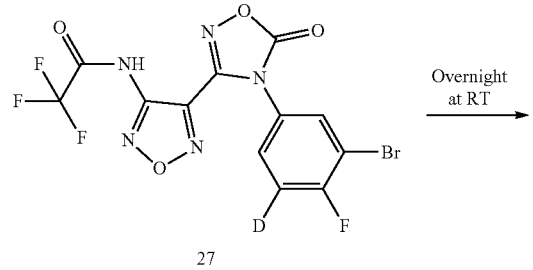

27

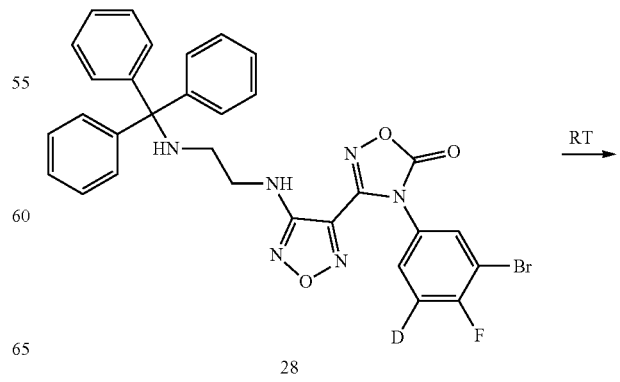

28

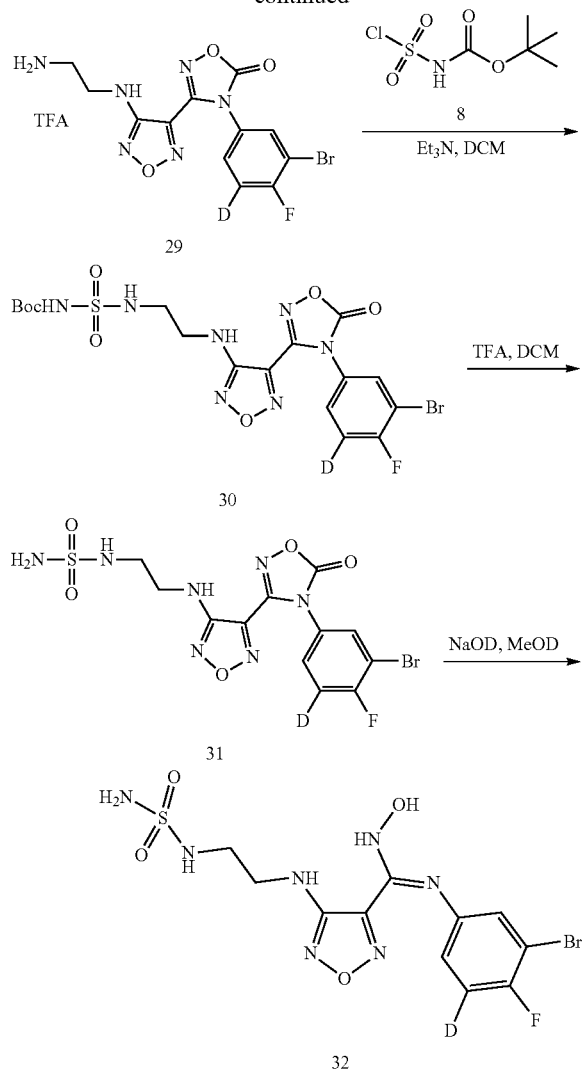

Step 4 Synthesis of Compound 27
The reaction procedure was the same as that of Example 2, Step 4, and 757 mg of a brown solid product was obtained with a yield of 91%. LC-MS (APCI): m/z=439.0 (M+1)⁺; ¹H NMR (300 MHz, DMSO-d₆) (δ/ppm) 7.95-7.92 (m, 1H), 7.56-7.53 (m, 1H).

Step 5 Synthesis of Compound 28
The reaction procedure was the same as that of Example 2, Step 5, and 805 mg of a yellow solid product was obtained with a yield of 75%. LC-MS (APCI): m/z=628.2 (M+1)⁺; ¹H NMR (300 MHz, DMSO-d₆) (δ/ppm) 11.49 (s, 1H), 8.88 (s, 1H), 7.12-7.09 (m, 1H), 6.77-6.75 (m, 1H), 6.70 (t, J=6.0 Hz, 1H), 6.59 (s, 2H), 6.24 (t, J=6.0 Hz, 1H), 3.37 (q, J=6.0 Hz, 2H), 3.11 (q, J=6.0 Hz, 2H).

Step 6 Synthesis of Compound 29
The reaction procedure was the same as that of Example 1, Step 4, and the resulting oily product was used directly in the next step. LC-MS (APCI): m/z=386.0 (M+1)⁺.

Step 7 Synthesis of Compound 31
The reaction procedure was the same as that of step 5 and step 6 in Example 1, and the resulting white solid product was used directly in the next step. LC-MS (APCI): m/z=465.1 (M+1)⁺.

Step 8 Synthesis of Compound 32
The reaction procedure was the same as that of Example 1, Step 7, and 111 mg of a yellow solid product was obtained. LC-MS (APCI): m/z=439.1 (M+1)⁺; ¹H NMR (300 MHz, DMSO-d₆) (δ/ppm) 11.49 (s, 1H), 8.88 (s, 1H), 7.12-7.09 (m, 1H), 6.77-6.75 (m, 1H), 6.70 (t, J=6.0 Hz, 1H), 6.59 (s, 2H), 6.24 (t, J=6.0 Hz, 1H), 3.37 (q, J=6.0 Hz, 2H), 3.11 (q, J=6.0 Hz, 2H).

Example 4

Preparation of 4-({2-[(sulfamoyl)amino]-2,2-d₂-ethyl}amino)-N-(3-bromo-4-fluorophenyl)-N'-hydroxy-1,2,5-oxadiazole-3-carboximidamide (Compound 41)

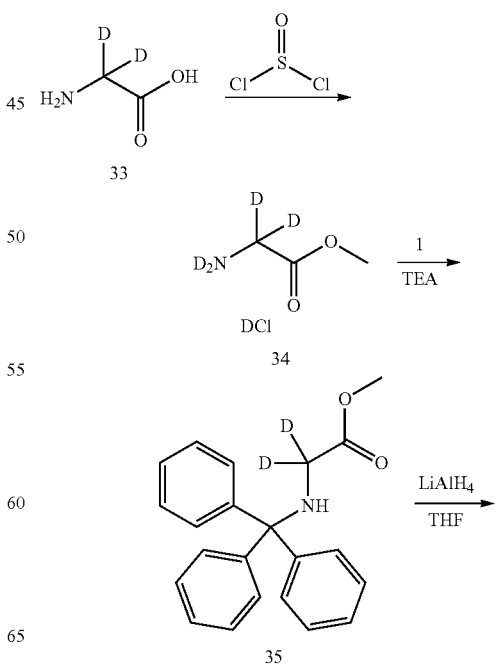

Step 1 Synthesis of Compound 24
Pd/C (50 mg) was added to a solution of 3,5-dibromo-4-fluoroaniline (1 g, 3.7 mmol) in MeOD (20 mL), and stirred under a D2 atmosphere for 2 hours. The organic phase was collected by filtration, and dissolved in dichloromethane. A saturated sodium bicarbonate solution was added. The collected organic phase was extracted with dichloromethane and purified by column to give 350 mg of a brown oily product. The yield was 50%. LC-MS (APCI): m/z=191.1 (M+1)⁺; ¹H NMR (300 MHz, DMSO-d₆) (δ/ppm) 6.80-6.77 (m, 1H), 6.54-6.50 (m, 1H), 5.20 (br s, 2H).

Step 2 Synthesis of Compound 25
The reaction procedure was the same as that of Example 2, Step 2, and 385 mg of a gray solid product was obtained with a yield of 66%. LC-MS (APCI): m/z=317.0 (M+1)⁺. ¹H NMR (300 MHz, DMSO-d₆) (δ/ppm) 11.42 (s, 1H), 8.86 (s, 1H), 7.11-7.08 (m, 1H), 6.76-6.74 (m, 1H), 6.24 (br s, 2H).

Step 3 Synthesis of Compound 26
The reaction procedure was the same as that of Example 2, Step 3, and 642 mg of a brown solid product was obtained with a yield of 98.5%. LC-MS (APCI): m/z=343.1.0 (M+1)⁺; ¹H NMR (300 MHz, DMSO-d₆) (δ/ppm) 8.09-8.06 (m, 1H), 7.72-7.69 (m, 1H), 6.60 (br s, 2H).

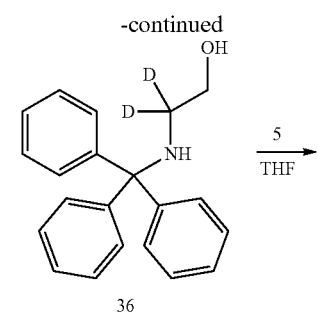

36

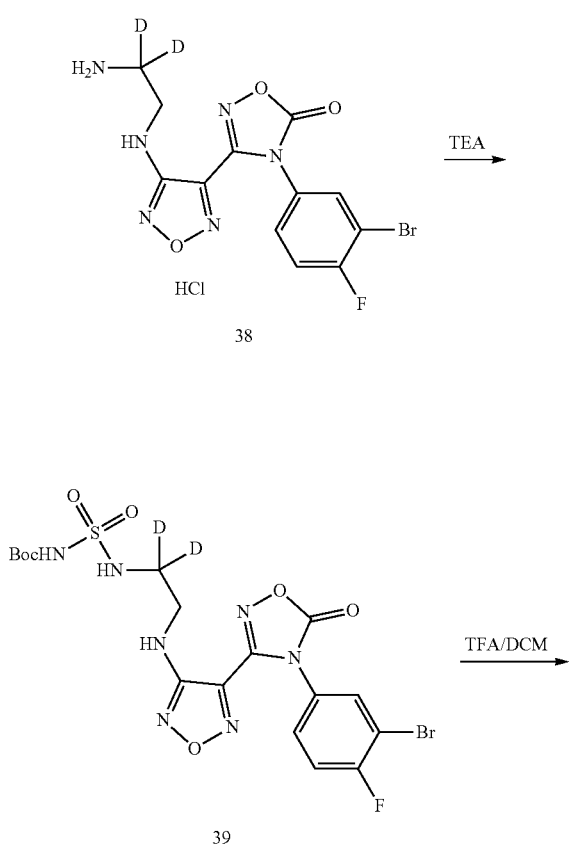

37

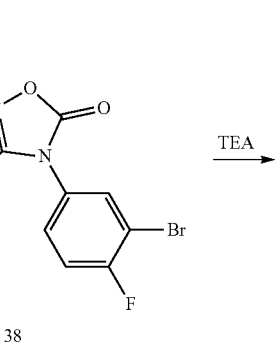

38

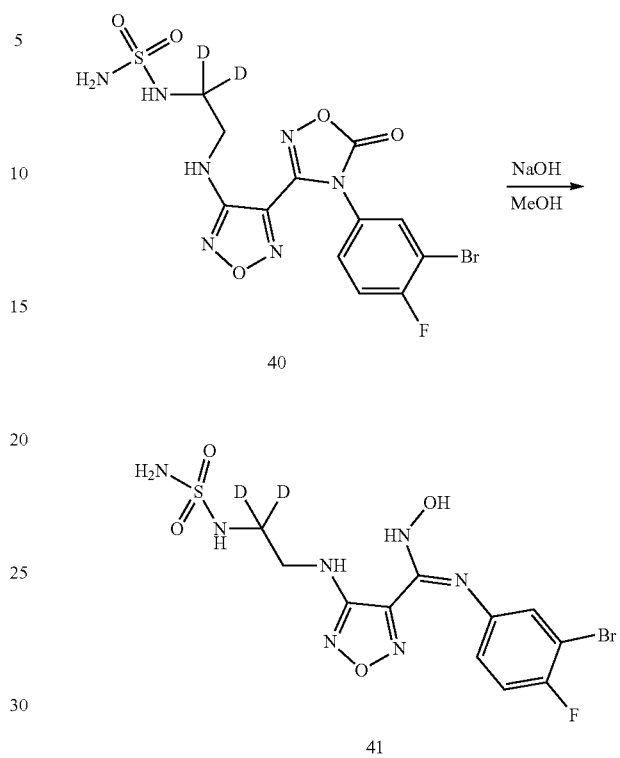

40

41

Step 1 Synthesis of Compound 34

After cooling a solution of the compound 33 (1.0 g, 12.97 mmol) in 10 mL of the deuterated methanol to 0° C., thionyl chloride (2.78 g, 23.35 mmol) was added slowly. After the addition, the mixture was stirred at room temperature for 2 hours and then heated to reflux temperature. The reaction was continued for 1.5 hours, and then cooled to room temperature. The solvent was removed. The residue was dried to obtain the title product as a white solid, 1.62 g in total, yield 97%. $^1$H NMR (300 MHz, CDCl$_3$) (δ/ppm) 3.84 (s, 3H).

Step 2 Synthesis of Compound 35

To a mixture of compound 34 (1.62 g, 12.6 mmol) and triethylamine (TEA, 2.55 g, 25.2 mmol) was added Triphenylmethyl chloride (3.86 g, 13.86 mmol). The reaction was heated to reflux for 6 hours. The mixture was cooled to room temperature. Water was added and stirred for 10 minutes. The organic phase was collected to obtain the title product as a white solid, 3.1 g in total, yield 73.8%.

Step 3 Synthesis of Compound 36

After cooling a solution of AlLiH$_4$ (228 mg, 6.00 mmol) in tetrahydrofuran (THF, 5 mL) to 0° C., compound 35 (1.0 g, 3 mmol) was added and stirred at room temperature for 30 minutes. 0.5 mL of water was added to quench the reaction. Ethyl acetate (15 mL) was added, and the mixture was stirred for 10 minutes and then filtered. The filtrate was collected by drying on a rotary evaporator and purified by column chromatography to give the title product as a white solid (800 mg in total, yield: 72.7%). $^1$H NMR (300 MHz, CDCl$_3$) (δ/ppm) 7.49 (d, 6H, J=6.3 Hz), 7.30 (t, 6H, J=5.4 Hz), 7.21 (t, 3H, 5.4 Hz), 3.70 (s, 2H).

Step 4 Synthesis of Compound 37

Compound 36 (488 mg, 1.60 mmol) and triphenylphosphine (419 mg, 1.60 mmol) were dissolved in 5 mL THF and cooled to 0° C. and diisopropyl azodicarboxylate (DIAD, 323 mg, 1.60 mmol) was added. After stirring at this temperature for 15 minutes, a solution of compound 5 (500 mg, 1.14 mmol) in THF (5 mL) was added, stirred at room temperature overnight, quenched with water, and extracted with ethyl acetate. The organic phase was collected and recrystallized to give the title product as a white solid with a total of 380 mg and a yield of 52.9%. LC-MS (APCI): m/z=629.2 (M+1)$^+$.

Step 5 Synthesis of Compound 38

Compound 37 (380 mg, 604 μmol) was added to a solution of triisopropylsilane (287 mg, 1.81 mmol) in trifluoroacetic acid (TFA, 3 mL), stirred at room temperature for 30 minutes, filtered, and washed with 2 mL of TFA. The filtrate was collected and dried on a rotary evaporator to obtain a solid, which was dissolved in 3 mL of MeOD. After adding 0.3 mL of hydrochloric acid/dioxane, the mixture was stirred at room temperature for 30 minutes. After removing the solvent, the title product was obtained as a white solid, 230 mg in total, with a yield of 89.8%. LC-MS (APCI): m/z=387.2 (M+1)$^+$; $^1$H NMR (300 MHz, CDCl$_3$) (δ/ppm) 7.64-7.62 (m, 2H), 7.36-7.29 (m, 4H), 3.01 (s, 2H).

Step 6 Synthesis of Compound 39

A solution of chlorosulfonyl isocyanate (154 mg, 1.09 mmol) in dichloromethane (1 mL) was cooled to 0° C. and then a solution of tert-butanol (80 mg, 1.09 mmol) in dichloromethane (1 mL) was added dropwise. The mixture was stirred at room temperature for 1 hour. A solution of compound 38 (230 mg, 543 μmol) and triethylamine (321 mg, 3.17 mmol) in 8 mL of dichloromethane was added to the above reaction solution, stirred at room temperature for 2 hours, dried on a rotary evaporator, and purified by column chromatography to give the title product as a white solid, 80 mg in total, yield 26.1%. LC-MS (APCI): m/z=566.2 (M+1)$^+$.

Step 7 Synthesis of Compound 40

Compound 39 (22 mg, 39 μmol) was dissolved in dichloromethane (2.5 mL), trifluoroacetic acid (0.5 mL) was added, and then the mixture was stirred at room temperature for 2 hours. The solvent was removed to obtain the title product, which was used directly in the next step. LC-MS (APCI): m/z=466.1 (M+1)$^+$.

Step 8 Synthesis of Compound 41

Compound 40 (16 mg, 39 μmol) was dissolved in 1.5 mL of MeOD, a solution of NaOH in D$_2$O (2 M, 0.5 mL, 1 mmol) was added and then the mixture was stirred at room temperature for 2 h. A solution of 6N HCl was added dropwise to adjust the pH to 7. The solvent was removed. The residue was separated and purified by column chromatography to give the title product as a white solid, 13 mg in total, with a yield of 76.5%. LC-MS (APCI): m/z=440.2 (M+1)$^+$; $^1$H NMR (300 MHz, DMSO-d$_6$) (δ/ppm) 11.47 (s, 1H), 8.86 (s, 1H), 7.16 (t, 1H, J=6.9 Hz), 7.09 (dd, 1H, J=4.5 Hz, 1.8 Hz), 6.75-6.73 (m, 1H), 6.65 (s, 1H), 6.55 (s, 2H), 6.18 (s, 1H), 3.33 (d, 1H, J=4.5 Hz), 3.07 (d, 1H, J=4.5 Hz).

Example 5

Preparation of 4-({2-[(sulfamoyl)amino]-1,1,2,2-d$_4$-ethyl}amino)-N-(3-bromo-4-fluorophenyl)-N'-hydroxy-1,2,5-oxadiazole-3-carboximidamide (Compound 47)

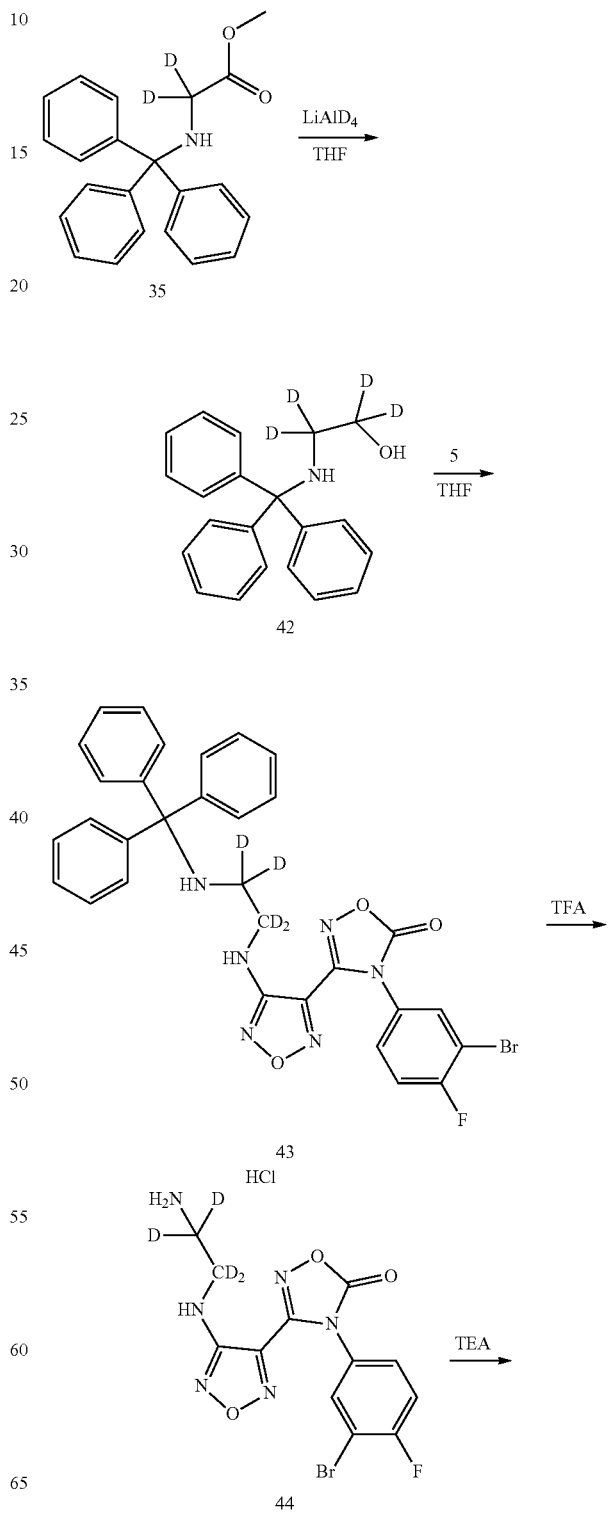

-continued

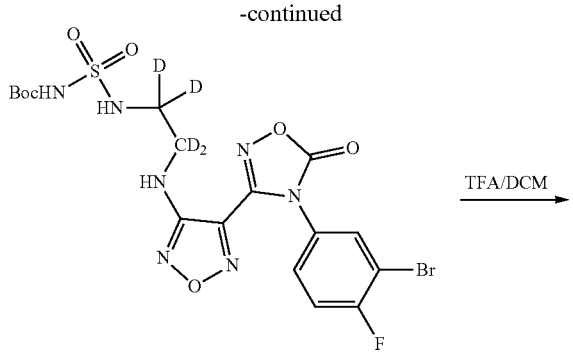

45

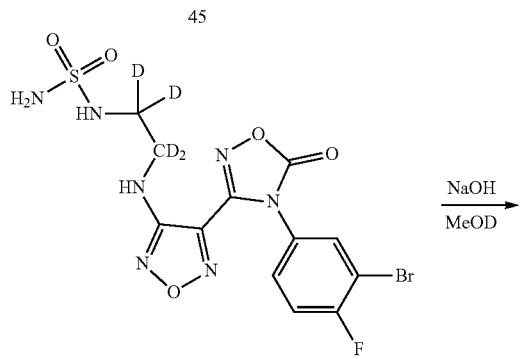

46

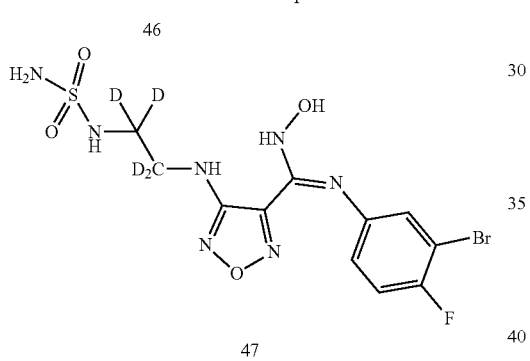

47

Step 1 Synthesis of Compound 42

Compound 35 (1.9 g, 5.7 mmol) was added to a solution of AlLiD$_4$ (359 mg, 8.55 mmol) in 5 mL of tetrahydrofuran at 0° C. After the addition was completed, the mixture was stirred at room temperature for 30 minutes. After 0.5 mL of water and 15 mL of ethyl acetate were added successively, stirring was continued for 10 minutes and the mixture was filtered. The filtrate was collected and purified by column to give 1.42 g of a white solid. The yield was 81.1%.

Step 2 Synthesis of Compound 43

The reaction procedure was the same as that of Example 4, Step 4, except that compound 42 was used instead of compound 36. Finally, 400 mg of a white solid product was obtained with a yield of 55.6%. LC-MS (APCI): m/z=631.2 (M+1)$^+$; $^1$H NMR (300 MHz, CDCl$_3$) (δ/ppm) 7.67 (dd, 1H, J=4.2 Hz, J2.1 Hz), 7.50 (d, 6H, J=6.0 Hz), 7.40-7.36 (m, 1H), 7.34-7.28 (m, 8H), 7.23 (t, 3H, J=5.4 Hz), 5.90 (s, 1H).

Step 3 Synthesis of Compound 44

The reaction procedure was the same as that of Example 4, Step 5, except that compound 43 was used instead of compound 37. Finally, 270 mg of a white solid product was obtained with a yield of 99%. LC-MS (APCI): m/z=389.2 (M+1)$^+$; $^1$H NMR (300 MHz, DMSO-d$_6$) (δ/ppm) 7.15 (dd, 1H, J=4.5 Hz, 1.5 Hz), 8.03 (s, 2H), 7.78-7.75 (m, 1H), 7.61 (t, 1H, J=6.3 Hz).

Step 4 Synthesis of Compound 45

The reaction procedure was the same as that of Example 4, Step 6, except that compound 44 was used instead of compound 38. Finally, 88 mg of a white solid product was obtained with a yield of 24.4%. LC-MS (APCI): m/z=568.2 (M+1)$^+$.

Step 5 Synthesis of Compound 46

The reaction procedure was the same as that of Example 4, Step 7, except that compound 45 was used instead of compound 39. Finally, a solid product was obtained, which was used directly in the next step. LC-MS (APCI): m/z=468.1 (M+1)$^+$.

Step 6 Synthesis of Compound 47

The reaction procedure was the same as that of Example 4, Step 8, except that compound 46 was used instead of compound 40. Finally, a white solid product (42 mg, yield 61.8%) was obtained. LC-MS (APCI): m/z=442.2 (M+1)$^+$; $^1$H NMR (300 MHz, DMSO-d$_6$) (δ/ppm) 11.50 (s, 1H), 8.89 (s, 1H), 7.18 (t, 1H, J=6.6 Hz), 7.12 (dd, 1H, J=4.2 Hz, 2.1 Hz), 6.79-6.75 (m, 1H), 6.67 (s, 1H), 6.58 (s, 2H), 6.21 (s, 1H).

Example 6

Preparation of 4-({2-[sulfamoyl)amino]-1,1,2,2-d$_4$-ethyl}amino)-N-(5-d-3-bromo-4-fluoro-phenyl)-N'-hydroxy-1,2,5-oxadiazole-3-carboximidamide (Compound 52)

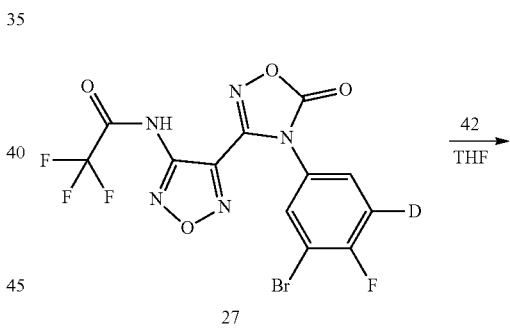

27

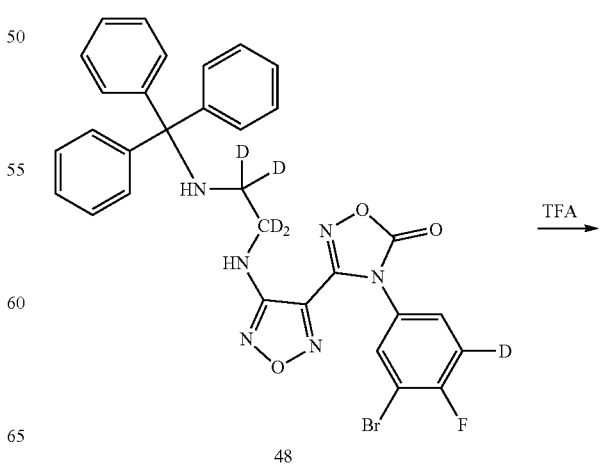

48

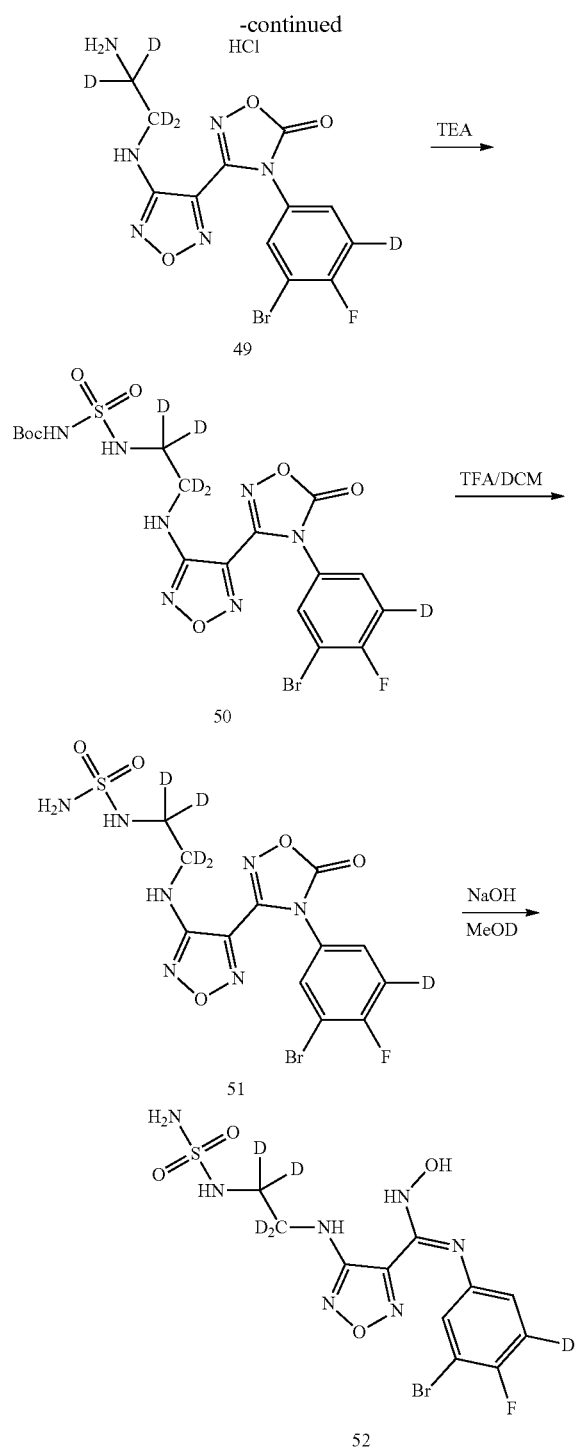

Step 2 Synthesis of Compound 49

The reaction procedure was the same as that of Example 4, Step 5, except that compound 48 was used instead of compound 37. Finally, 170 mg of a white solid product was obtained with a yield of 93.4%. LC-MS (APCI): m/z=390.1 (M+1)$^+$.

Step 3 Synthesis of Compound 50

The reaction procedure was the same as that of Example 4, Step 6, except that compound 49 was used instead of compound 38. Finally, a white solid product (140 mg) was obtained with a yield of 61.7%. LC-MS (APCI): m/z=569.2 (M+1)$^+$; $^1$H NMR (300 MHz, DMSO-d$_6$) (δ/ppm) 10.90 (s, 1H), 8.09 (dd, 1H, J=4.5 Hz, 2.1 Hz), 7.72 (dd, 1H, J=3.0 Hz, 1.8 Hz), 7.70 (s, 1H), 6.57 (s, 1H), 1.41 (s, 9H).

Step 4 Synthesis of Compound 51

The reaction procedure was the same as that of Example 4, Step 7, except that compound 50 was used instead of compound 39. Finally, a solid product was obtained, which was used directly in the next step. LC-MS (APCI): m/z=469.1 (M+1)$^+$.

Step 5 Synthesis of Compound 52

The reaction procedure was the same as that of Example 4, Step 8, except that compound 51 was used instead of compound 40. Finally, 472 mg of a white solid product was obtained with a yield of 69.9%. LC-MS (APCI): m/z=443.2 (M+1)$^+$; $^1$HNMR (300 MHz, DMSO-d$_6$) (δ/ppm) 11.50 (s, 1H), 8.88 (s, 1H), 7.12 (dd, 1H, J=4.8 Hz, 2.1 Hz), 6.77 (t, 1H, J=2.7 Hz), 6.68 (s, 1H), 6.58 (s, 2H), 6.21 (s, 1H).

Example 7

Preparation of 4-({2-[(sulfamoyl)amino]-1,1,2,2-d$_4$-ethyl}amino)-N-(2,6-d$_2$-3-bromo-4-fluoro-phenyl)-N'-hydroxy-1,2,5-oxadiazole-3-carboximidamide (Compound 57)

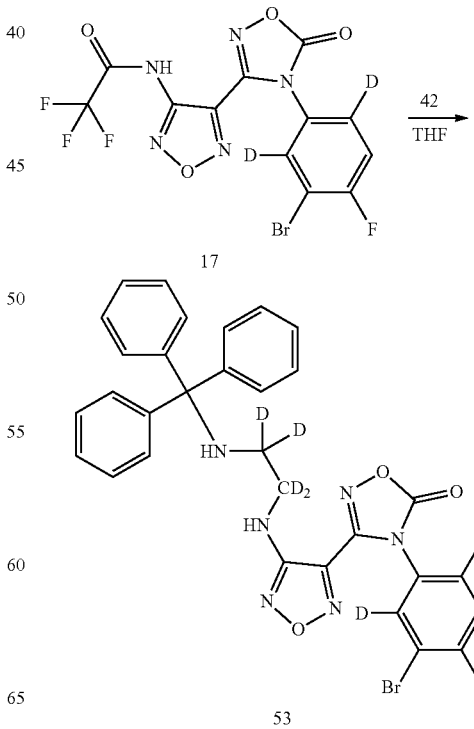

Step 1 Synthesis of Compound 48

The reaction procedure was the same as that of Example 4, Step 4, except that compound 42 was used instead of compound 36 and compound 27 was used instead of compound 5. Finally, 275 mg of a white solid product was obtained with a yield of 38.1%. LC-MS (APCI): m/z=632.2 (M+1)$^+$; $^1$HNMR (300 MHz, DMSO-d$_6$) (δ/ppm) 8.05 (dd, 1H, J=4.5 Hz, 1.5 Hz), 7.65 (dd, 1H, J=3.3 Hz, 1.8 Hz), 7.32 (d, 6H, J=6.0 Hz), 7.20 (t, 6H, J=6.0 Hz), 7.09 (t, 3H, J=5.4 Hz), 6.49 (s, 1H).

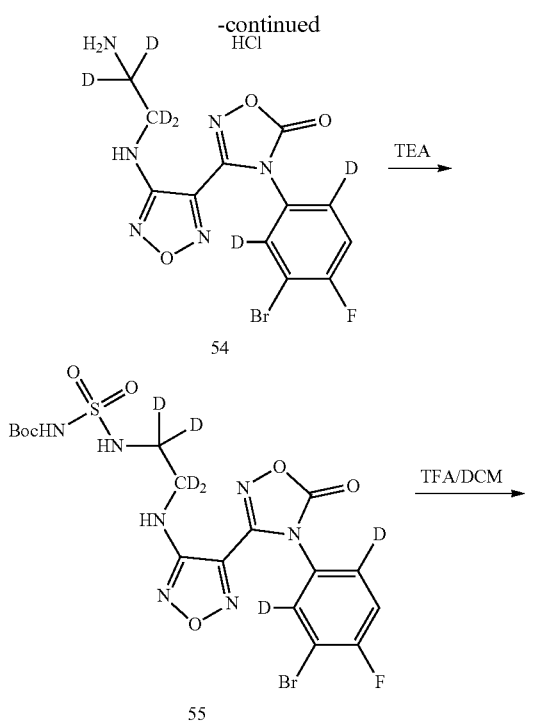

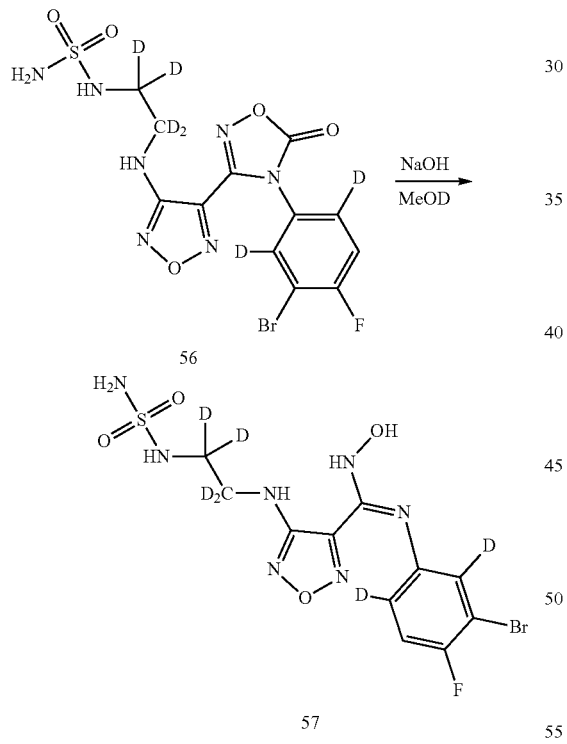

Step 1 Synthesis of Compound 53

The reaction procedure was the same as that of Example 4, Step 4, except that compound 42 was used instead of compound 36 and compound 17 was used instead of compound 5. Finally, 357 mg of a white solid product was obtained with a yield of 49.7%. LC-MS (APCI): m/z=633.3 (M+1)$^+$.

Step 2 Synthesis of Compound 54

The reaction procedure was the same as that of Example 4, Step 5, except that compound 53 was used instead of compound 37. Finally, 225 mg of a white solid product was obtained with a yield of 93.4%. LC-MS (APCI): m/z=391.1 (M+1)$^+$; $^1$H NMR (300 MHz, DMSO-d$_6$) (δ/ppm) 8.02 (s, 2H), 7.61 (d, 1H, J=6.6 Hz), 6.75 (s, 1H).

Step 3 Synthesis of Compound 55

The reaction procedure was the same as that of Example 4, Step 6, except that compound 54 was used instead of compound 38. Finally, 225 mg of a white solid product was obtained with a yield of 76.8%. LC-MS (APCI): m/z=570.2 (M+1)$^+$.

Step 4 Synthesis of Compound 56

The reaction procedure was the same as that of Example 4, Step 7, except that compound 55 was used instead of compound 39. Finally, a solid product was obtained, which was used directly in the next step. LC-MS (APCI): m/z=470.1 (M+1)$^+$.

Step 5 Synthesis of Compound 57

The reaction procedure was the same as that of Example 4, Step 8, except that compound 56 was used instead of compound 40. Finally, 130 mg of a white solid product was obtained with a yield of 74.5%. LC-MS (APCI): m/z=445.2 (M+1)$^+$; $^1$H NMR (300 MHz, DMSO-d$_6$) (δ/ppm) 11.49 (s, 1H), 8.88 (s, 1H), 7.18 (d, 1H, J=6.6 Hz), 6.67 (s, 1H), 6.57 (s, 2H), 6.21 (s, 1H).

Example 8

Preparation of 4-({2-[sulfamoyl)amino]-ethyl}amino)-N-(2,5,6-d$_3$-3-bromo-4-fluoro-phenyl)-N'-hydroxy-1,2,5-oxadiazole-3-carboximidamide (Compound 65)

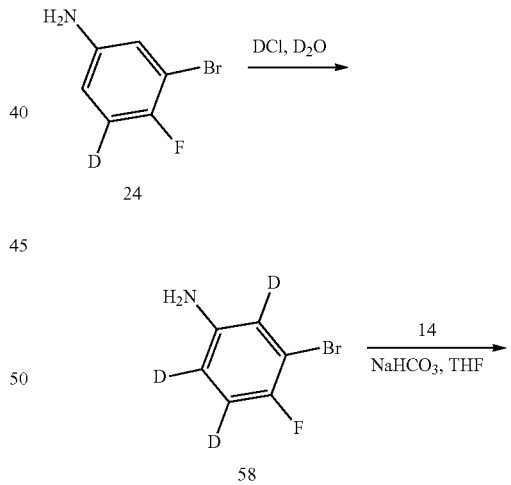

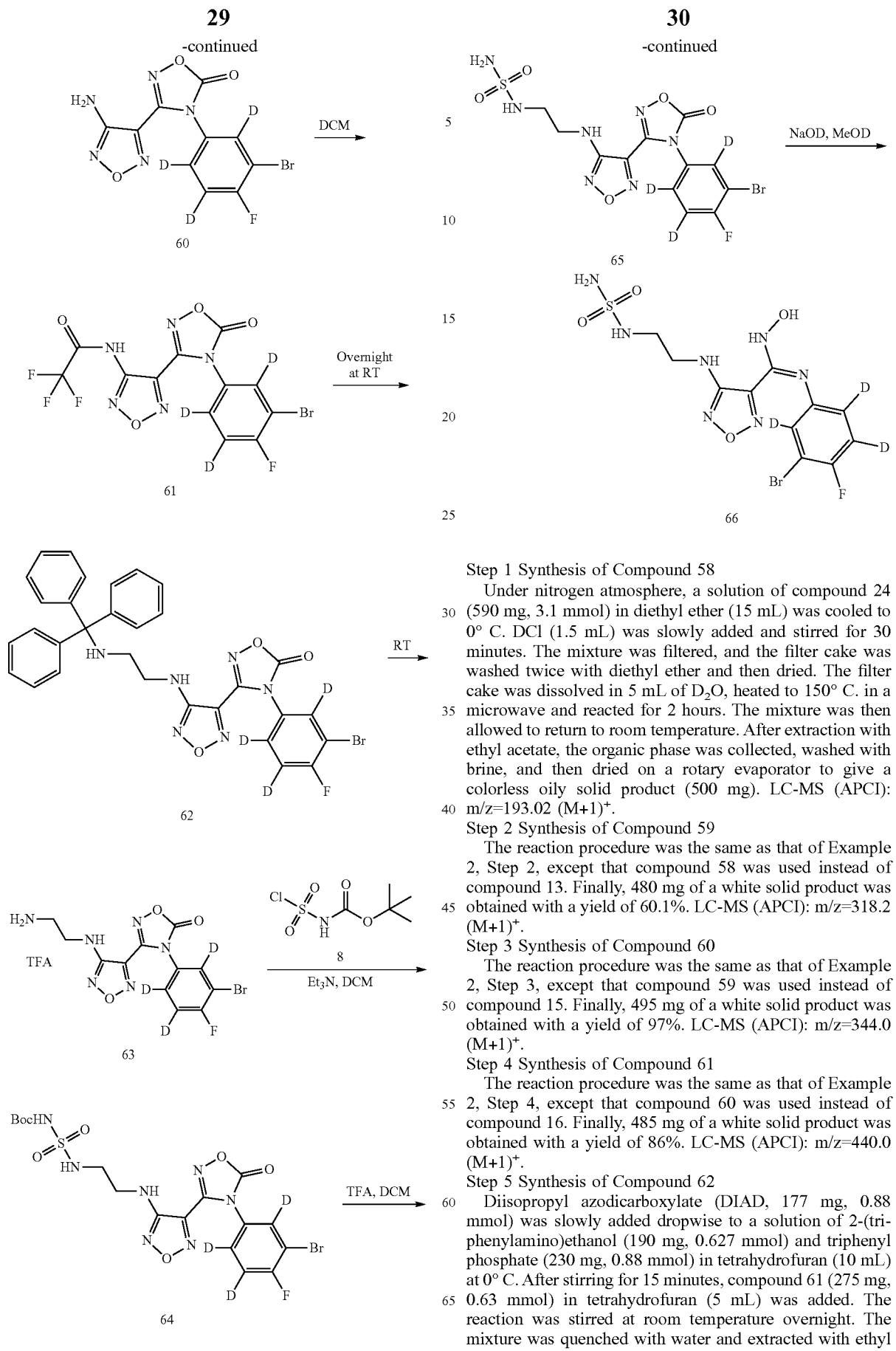

Step 1 Synthesis of Compound 58

Under nitrogen atmosphere, a solution of compound 24 (590 mg, 3.1 mmol) in diethyl ether (15 mL) was cooled to 0° C. DCl (1.5 mL) was slowly added and stirred for 30 minutes. The mixture was filtered, and the filter cake was washed twice with diethyl ether and then dried. The filter cake was dissolved in 5 mL of D$_2$O, heated to 150° C. in a microwave and reacted for 2 hours. The mixture was then allowed to return to room temperature. After extraction with ethyl acetate, the organic phase was collected, washed with brine, and then dried on a rotary evaporator to give a colorless oily solid product (500 mg). LC-MS (APCI): m/z=193.02 (M+1)$^+$.

Step 2 Synthesis of Compound 59

The reaction procedure was the same as that of Example 2, Step 2, except that compound 58 was used instead of compound 13. Finally, 480 mg of a white solid product was obtained with a yield of 60.1%. LC-MS (APCI): m/z=318.2 (M+1)$^+$.

Step 3 Synthesis of Compound 60

The reaction procedure was the same as that of Example 2, Step 3, except that compound 59 was used instead of compound 15. Finally, 495 mg of a white solid product was obtained with a yield of 97%. LC-MS (APCI): m/z=344.0 (M+1)$^+$.

Step 4 Synthesis of Compound 61

The reaction procedure was the same as that of Example 2, Step 4, except that compound 60 was used instead of compound 16. Finally, 485 mg of a white solid product was obtained with a yield of 86%. LC-MS (APCI): m/z=440.0 (M+1)$^+$.

Step 5 Synthesis of Compound 62

Diisopropyl azodicarboxylate (DIAD, 177 mg, 0.88 mmol) was slowly added dropwise to a solution of 2-(triphenylamino)ethanol (190 mg, 0.627 mmol) and triphenyl phosphate (230 mg, 0.88 mmol) in tetrahydrofuran (10 mL) at 0° C. After stirring for 15 minutes, compound 61 (275 mg, 0.63 mmol) in tetrahydrofuran (5 mL) was added. The reaction was stirred at room temperature overnight. The mixture was quenched with water and extracted with ethyl acetate. The organic phase was collected and purified by column chromatography. This was followed by recrystallization. 90 mg of a white solid product was obtained with a yield of 30.4%. LC-MS (APCI): m/z=630.3 (M+1)$^+$.

Step 6 Synthesis of Compound 63

Triisopropylsilane (68 mg, 429 mmol) was dissolved in trifluoroacetic acid (2.5 mL), compound 62 (90 mg, 143 μmol) was added, and the mixture was stirred at room temperature for 1 hour and filtered. The filter cake was washed with 2 mL of trifluoroacetic acid and the filtrate was collected and dissolved in 5 mL of MeOD. Hydrochloric acid:dioxane (1:1, 0.5 mL) was added and the mixture was stirred at room temperature for 30 minutes. The solvent was removed. Diethyl ether was added to the residue, and then the filtrate was collected to obtain 70 mg of a white solid product with a yield of 94.4%. LC-MS (APCI): m/z=388.1 (M+1)$^+$.

Step 7 Synthesis of Compound 64

A solution of compound 8 (51 mg, 0.358 mmol) in 10 mL of dichloromethane was cooled to 0° C. and a solution of tert-butanol (27 mg, 0.358 mmol) in dichloromethane (1 mL) was added dropwise. After the addition was complete, the reaction was stirred at room temperature for 1 hour. A solution of compound 63 (70 mg, 165 μmol) and triethylamine (73 mg, 0.716 mmol) in dichloromethane (15 mL) was added and stirring was continued at room temperature for 2 hours. The solvent was removed and the residue was purified by column to give the title product (70 mg) with a yield of 74.2%. LC-MS (APCI): m/z=567.2 (M+1)$^+$.

Step 8 Synthesis of Compound 65

Compound 64 (70 mg, 123 μmol) was dissolved in dichloromethane (5 mL), 1 mL of trifluoroacetic acid was added, and the mixture was stirred at room temperature for 1 hour. After removing the solvent, the product was obtained and used directly in the next step. LC-MS (APCI): m/z=467.1 (M+1)$^+$.

Step 9 Synthesis of Compound 66

After the compound 65 obtained in the previous step was dissolved in 2 mL of MeOD, 2 M NaOH (0.5 mL, 1 mmol) was added and the mixture was stirred at room temperature for 2 hours. The pH of the reaction solution was adjusted to neutrality by adding 6N HCl. The solvent was removed, and the residue was separated and purified by column chromatography to obtain 85 mg of the title product with a yield of 64.6%. LC-MS (APCI): m/z=441.2 (M+1)$^+$; $^1$H NMR (300 MHz, DMSO-d$_6$) (δ/ppm) 11.60 s, 1H), 8.98 (s, 1H), 6.80 (t, J=6.0 Hz, 1H), 6.68 (s, 2H), 6.33 (t, J=6.0 Hz, 1H), 3.47 (q, J=6.0 Hz, 2H), 3.21 (q, J=6.0 Hz, 2H).

Example 9

Preparation of 4-({2-[(sulfamoyl)amino]-1,1,2,2-d$_4$-ethyl}amino)-N-(2,5,6-d$_3$-3-bromo-4-fluoro-phenyl)-N'-hydroxy-1,2,5-oxadiazole-3-carboximidamide (Compound 71)

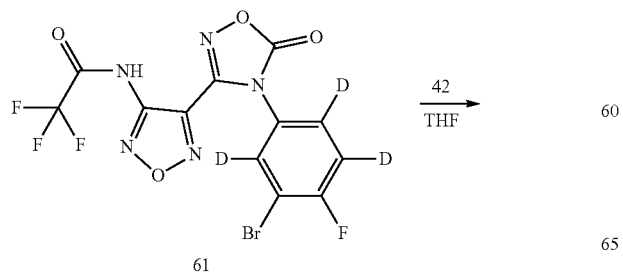

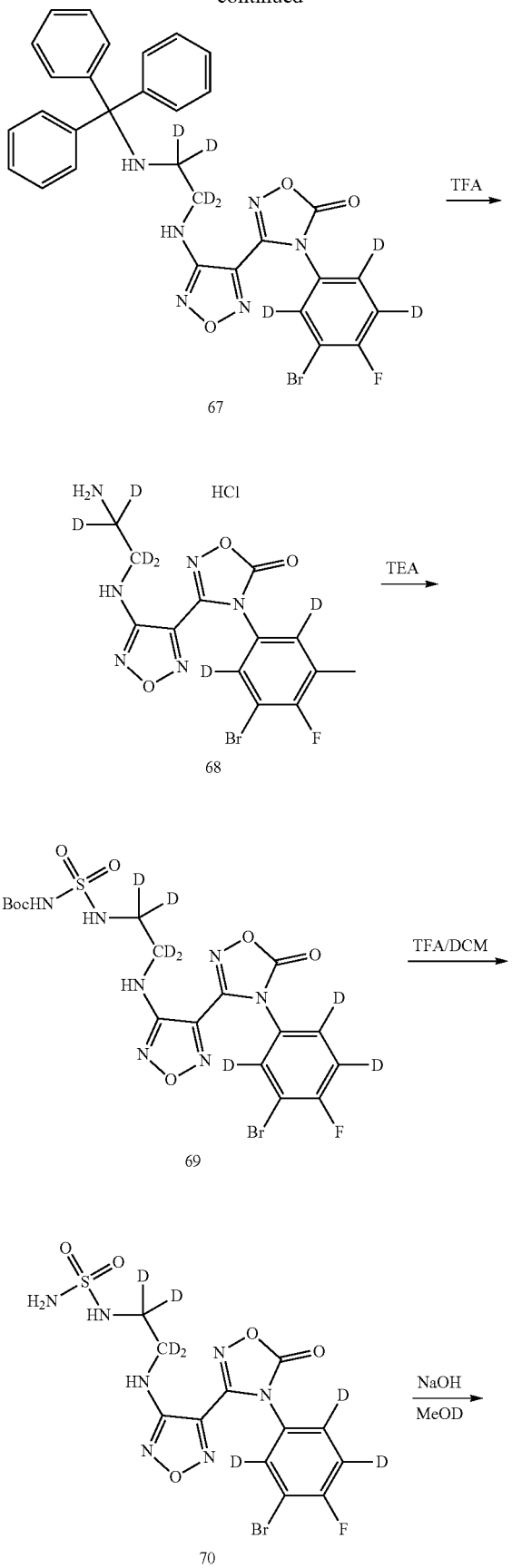

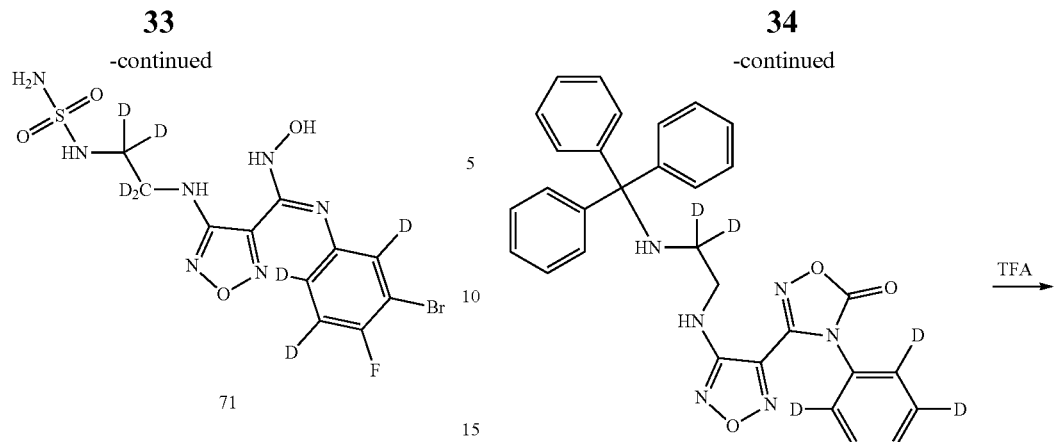

71

Step 1 Synthesis of Compound 67
The reaction procedure was the same as that of Example 4, Step 4, except that compound 42 was used instead of compound 36, and compound 61 was used instead of compound 5. Finally, 280 mg of a white solid product was obtained with a yield of 38.9%. LC-MS (APCI): m/z=634.3 (M+1)$^+$.

Step 2 Synthesis of Compound 68
The reaction procedure was the same as that of Example 4, Step 5, except that compound 67 was used instead of compound 37. Finally, 186 mg of a white solid product was obtained with a yield of 98.4%. LC-MS (APCI): m/z=392.1 (M+1)$^+$.

Step 3 Synthesis of Compound 69
The reaction procedure was the same as that of Example 4, Step 6, except that compound 68 was used instead of compound 38. Finally, 180 mg of a white solid product was obtained with a yield of 72.6%. LC-MS (APCI): m/z=571.2 (M+1)$^+$.

Step 4 Synthesis of Compound 70
The reaction procedure was the same as that of Example 4, Step 7, except that compound 69 was used instead of compound 39. Finally, a solid product was obtained, which was used directly in the next step. LC-MS (APCI): m/z=471.1 (M+1)$^+$.

Step 5 Synthesis of Compound 71
The reaction procedure was the same as that of Example 4, Step 8, except that compound 70 was used instead of compound 40. Finally, 80 mg of a white solid product was obtained with a yield of 57.1%. LC-MS (APCI): m/z=445.2 (M+1)$^+$; $^1$H NMR (300 MHz, DMSO-d$_6$) (δ/ppm) 11.49 (s, 1H), 8.88 (s, 1H), 6.67 (s, 1H), 6.57 (s, 2H), 6.20 (s, 1H).

Example 10

Preparation of 4-({2-[(sulfamoyl)amino]-1,1-d$_2$-ethyl}amino)-N-(2,5,6-d$_3$-3-bromo-4-fluoro-phenyl)-N'-hydroxy-1,2,5-oxadiazole-3-carboximidamide (Compound 76)

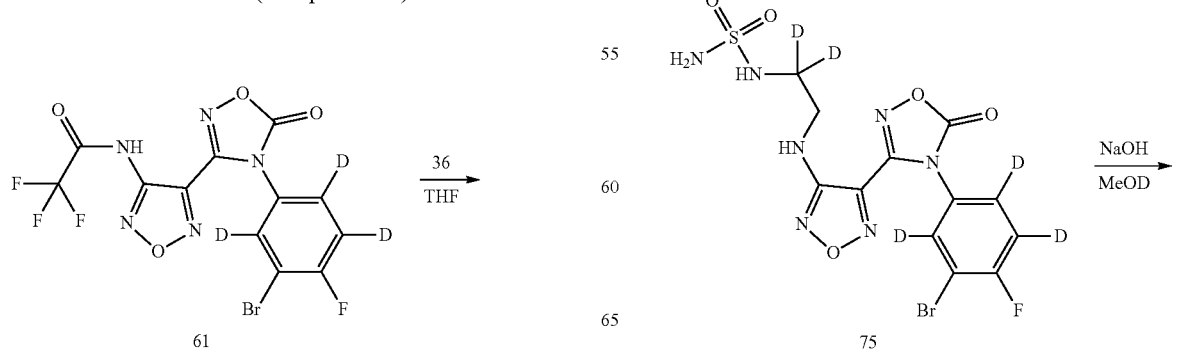

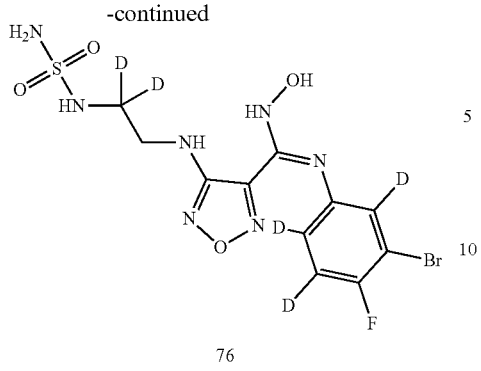

76

Step 1 Synthesis of Compound 72
The reaction procedure was the same as that of Example 4, Step 4, except that compound 61 was used instead of compound 5. Finally, 430 mg of a white solid product was obtained with a yield of 59.6%. LC-MS (APCI): m/z=632.3 (M+1)$^+$.

Step 2 Synthesis of Compound 73
The reaction procedure was the same as that of Example 4, Step 5, except that compound 72 was used instead of compound 37. Finally, 280 mg of a white solid product was obtained with a yield of 96.6%. LC-MS (APCI): m/z=390.1 (M+1)$^+$.

Step 3 Synthesis of Compound 74
The reaction procedure was the same as that of Example 4, Step 6, except that compound 73 was used instead of compound 38. Finally, 270 mg of a white solid product was obtained with a yield of 72.4%. LC-MS (APCI): m/z=569.2 (M+1)$^+$.

Step 4 Synthesis of Compound 75
The reaction procedure was the same as that of Example 4, Step 7, except that compound 74 was used instead of compound 39. Finally, a solid product was obtained, which was used directly in the next step. LC-MS (APCI): m/z=469.1 (M+1)$^+$.

Step 5 Synthesis of Compound 76
The reaction procedure was the same as that of Example 4, Step 8, except that compound 75 was used instead of compound 40. Finally, 170 mg of a white solid product was obtained with a yield of 81.7%. LC-MS (APCI): m/z=443.2 (M+1)$^+$; $^1$H NMR (300 MHz, DMSO-d$_6$) (δ/ppm) 11.47 (s, 1H), 8.86 (s, 1H), 6.66 (s, 1H), 6.55 (s, 2H), 6.19 (s, 1H), 3.33 (d, 1H, J=4.5 Hz), 3.07 (d, 1H, J=4.2 Hz).

Example 11

Preparation of 4-({2-[(sulfamoyl)amino]-1,1-d2-ethyl}amino)-N-(2,6-d$_2$-3-bromo-4-fluoro-phenyl)-N'-hydroxy-1,2,5-oxadiazole-3-carboximidamide (Compound 81)

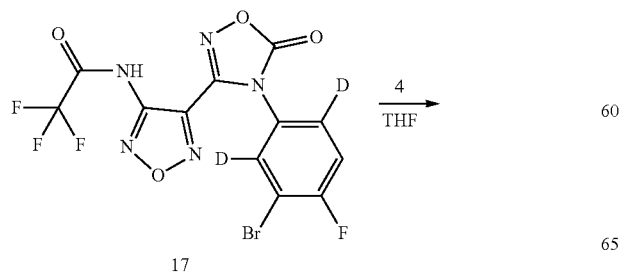

17

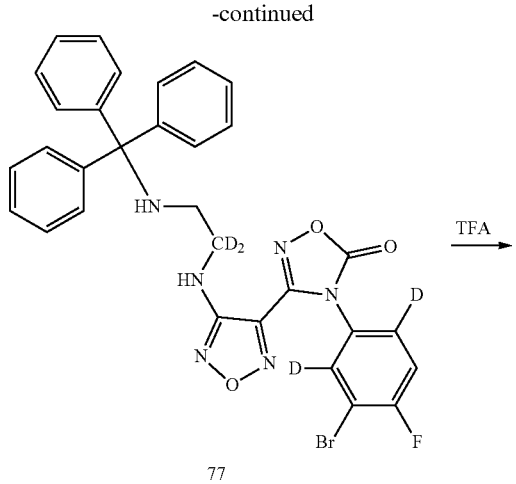

77

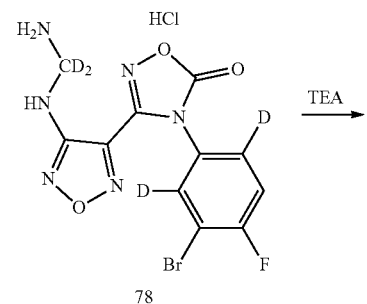

78

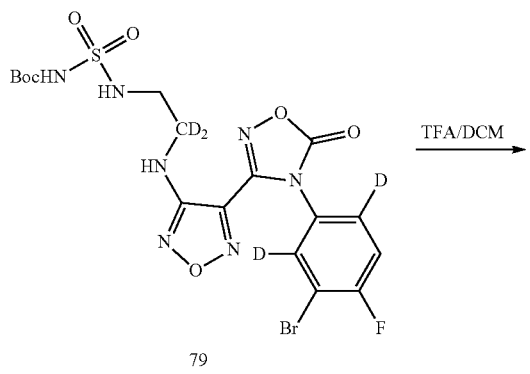

79

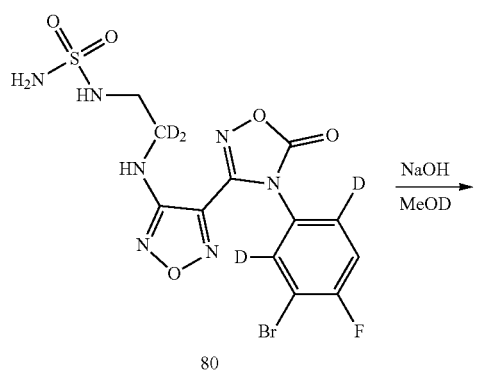

80

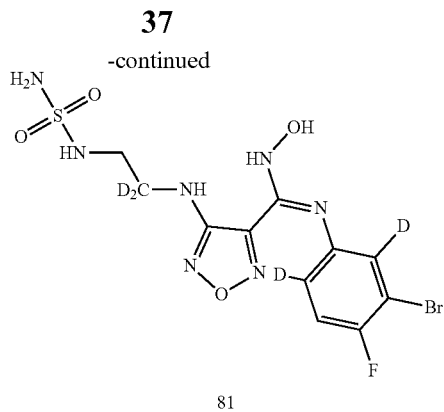

81

Step 1 Synthesis of Compound 77

After cooling a solution of the compound 4 (488 mg, 1.60 mmol) and triphenyl phosphate (419 mg, 1.60 mmol) in 10 mL of tetrahydrofuran to 0° C., DIAD (323 mg, 1.60 mmol) was added and stirred at this temperature for 15 minutes. A solution of compound 17 (500 mg, 1.14 mmol) in 5 mL of tetrahydrofuran was added and stirred at room temperature overnight. Water was added and the mixture was extracted with ethyl acetate. The organic phase was collected and purified by recrystallization from methyl tert-butyl ether to give 400 mg of a white solid. The yield was 55.4%. LC-MS (APCI): m/z=631.3 (M+1)$^+$.

Step 2 Synthesis of Compound 78

Compound 77 (220 mg, 349 μmol) was added to a solution of triisopropylsilane (165 mg, 1.05 mmol) in 4 mL of trifluoroacetic acid, and stirred at room temperature for 30 minutes. The mixture was filtered, the filter cake was washed with trifluoroacetic acid, and the filtrate was collected. The collected filtrate was dissolved in 5 mL of MeOD, and hydrochloric acid:dioxane (1:1, 0.5 mL) was added. The mixture was stirred at room temperature for 30 minutes. The solvent was removed. Diethyl ether was added to the residue and the filtrate was collected to obtain a white solid product (140 mg). The yield was 94.6%. LC-MS (APCI): m/z=389.1 (M+1)$^+$.

Step 3 Synthesis of Compound 79

A solution of compound 8 (101 mg, 0.716 mmol) in 10 mL of dichloromethane was cooled to 0° C. and a solution of tert-butanol (53 mg, 0.716 mmol) in dichloromethane (1 mL) was added dropwise. After the addition was complete, the reaction was stirred at room temperature for 1 hour. A solution of compound 78 (140 mg, 330 μmol) and triethylamine (145 mg, 1.432 mmol) in dichloromethane (15 mL) was added, and the mixture was further stirred at room temperature for 2 hours. The solvent was removed and the residue was purified by column to obtain 135 mg of the title product with a yield of 72.2%. LC-MS (APCI): m/z=568.2 (M+1)$^+$.

Step 4 Synthesis of Compound 80

Compound 79 (135 mg, 238 μmol) was dissolved in dichloromethane (5 mL), 1 mL of trifluoroacetic acid was added, and the mixture was stirred at room temperature for 1 hour. After the solvent was removed, the product was obtained and used directly in the next step. LC-MS (APCI): m/z=468.1 (M+1)$^+$.

Step 9 Synthesis of Compound 81

The compound 80 obtained in the previous step was dissolved in 4 mL of MeOD, 2 M NaOH (1.5 mL, 3 mmol) was added, and the mixture was stirred at room temperature for 2 hours. The pH of the reaction solution was adjusted to neutral by adding 6N HCl. The solvent was removed, and the residue was separated and purified by column chromatography to give 85 mg of the title product with a yield of 63%. LC-MS (APCI): m/z=442.2 (M+1)$^+$; $^1$H NMR (300 MHz, DMSO-d$_6$) (δ/ppm) 11.49 (s, 1H), 8.88 (s, 1H), 7.17 (d, J=8.8 Hz, 1H), 6.71 (t, J=6.0 Hz, 1H), 6.59 (s, 2H), 6.24 (t, J=6.0 Hz, 1H), 3.37 (d, J=5.6 Hz, 1H), 3.11 (d, J=5.6 Hz, 1H).

Biological Activity Test.

Indoleamine 2,3-dioxygenase Assay

Human indoleamine 2,3-dioxygenase (IDO) with an N-terminal His tag was expressed in *E. coli* and purified to homogeneity. IDO catalyzes the oxidative cleavage of the pyrrole ring of the indole nucleus of tryptophan to give N'-formyl kynurenine. As described in the literature (M. Sono et. al., J. Biol. Chem. 1980, 255, 1339-1345), at room temperature, the assay was performed using 95 nM IDO and 2 mM D-Trp in the presence of 50 mM potassium phosphate buffer (pH 6.5) with 20 mM ascorbate, 5 μM methylene blue and 0.2 mg/mL hydrogen peroxidase. After an increase in absorbance at 321 nm (due to the formation of N'-formyl kynurenine), the initial reaction rate was continuously recorded. The experimental results are shown in Table 1 below, in which A represents IC$_{50}$≤50 nM and B represents 50 nM<IC$_{50}$<100 nM. Epacadostat is the world's first and currently best-performing small molecule IDO inhibitor developed by the US drug company Incyte.

TABLE 1

| Inhibition of IDO Enzymes by example compounds | | | |
|---|---|---|---|
| Number | IC$_{50}$ | Number | IC$_{50}$ |
| Compound 11 | A | Compound 22 | A |
| Compound 32 | A | Compound 41 | A |
| Compound 47 | A | Compound 52 | A |
| Compound 57 | A | Compound 66 | A |
| Compound 71 | A | Compound 76 | A |
| Compound 81 | B | Epacadostat | B |

The experimental results are shown in Table 1 above. The compounds disclosed herein have a significant inhibitory effect on the IDO1 enzyme, wherein compound 81 has an equivalent inhibitory effect as that of Epacadostat, and compound 11, compound 22, compound 32, compound 41, compound 47, compound 52, compound 57, compound 66, compound 71 and compound 76 have even better inhibitory effects than that of Epacadostat.

Indoleamine 2,3-dioxygenase Cell Experiment

HeLa cells (#CCL-2, ATCC) were kept in minimal basal medium (eagle) containing 2 mM L-glutamine and Earle's BSS formulated to contain 1.5 g/L sodium bicarbonate, 0.1 mM non-essential amino acids, 1 mM sodium pyruvate, and 10% fetal calf serum (all purchased from Invitrogen). Cells were stored at 37° C. in a humidity controlled incubator providing 5% CO$_2$. The assay was performed as follows: HeLa cells were seeded in a 96-well culture plate at a density of 5×10$^3$/well and cultured overnight. The following day, IFN-γ (50 ng/mL final concentration) and serial dilution solutions of compound (a total volume of 200 μL medium) were added to the cells. After 48 hours of incubation, 140 μL of supernatant/well was transferred to a new 96-well plate. 10 μL of 6.1N trichloroacetic acid (#T0699, Sigma) was mixed in each well and incubated at 50° C. for 30 minutes to hydrolyze the N-formyl kynurenine produced by the indoleamine 2,3-dioxygenase into Kynurenine. The reaction mixture was then centrifuged at 2500 rpm for 10 minutes to remove the precipitate. 100 μL of supernatant/well was transferred to another 96 well plate and mixed with 100 μL of 2% (w/v) p-dimethylaminobenzaldehyde (#15647-7, Sigma-Aldrich) in acetic acid. The yellow color produced by kynurenine was measured at 480 nm using a SPECTRAmax 250 microplate reader (Molecular Devices). L-kynurenine (#K8625, Sigma) was used as a standard. Standard solutions (240, 120, 60, 30, 15, 7.5, 3.75, 1.87 μM) were prepared with 100 μL of medium and mixed with an equal volume of 2% (w/v) p-dimethylaminobenzaldehyde. The percentage of inhibition at each concentration was determined and average value was obtained in duplicate. Analysis of the data using non-linear regression, the obtained $IC_{50}$ values (Prism Graphpad) are shown in Table 2 below, wherein A denotes $IC_{50} \leq 5$ nM and B denotes 5 nM$<IC_{50} \leq 10$ nM. (Reference: Takikawa O, et. al., 1988, J. Biol. Chem., 263(4): 2041-8)

TABLE 2

Effect of example compounds on IDO cells

| Number | $IC_{50}$ | Number | $IC_{50}$ |
|---|---|---|---|
| Compound 11 | B | Compound 22 | B |
| Compound 32 | A | Compound 41 | A |
| Compound 47 | B | Compound 52 | B |
| Compound 57 | B | Compound 66 | B |
| Compound 71 | A | Compound 76 | A |
| Compound 81 | B | Epacadostat | B |

The experimental results are shown in Table 2 above. The compounds disclosed herein also exhibit excellent effects at the cellular level, wherein the compound 11, compound 22, compound 47, compound 52, compound 57, compound 66, and compound 81 have equivalent inhibitory effects to that of Epacadostat, while compound 32, compound 41, compound 71, and compound 76 have even better inhibitory effects than that of Epacadostat. This indicates that the compounds disclosed herein can be used as excellent IDO inhibitors for the preparation of a medicament for treating IDO-related diseases.

Metabolic Stability Evaluation

Experiments in microsomes: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: Powder of the example compound was accurately weighed and dissolved in DMSO to 5 mM.

Preparation of phosphate buffer (100 mM, pH7.4): A pre-formulated 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-PD, 3.3 mM magnesium chloride) was prepared and placed on wet ice prior to use.

Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, and mixed to obtain a liver microsome dilution solution with a protein concentration of 0.625 mg/mL. 25057.5 μL of phosphate buffer (pH 7.4) was taken into a 50 mL centrifuge tube, to which 812.5 μL SD rat liver microsomes were added, and mixed to obtain a liver microsome dilution solution with a protein concentration of 0.625 mg/mL.

Incubation of the samples: The stock solution of the respective compound was respectively diluted to 0.25 mM with an aqueous solution containing 70% acetonitrile, and used as a working solution, ready for use. 398 μL of the dilution solution of human liver microsomes or rat liver microsome were added to a 96-well incubation plate (N=2), respectively, and 2 μL of 0.25 mM working solution was added and mixed.

Metabolic stability assay: 300 μL of pre-chilled stop solution was added to each well of a 96-well deep well plate and placed on ice as a stop plate. The 96 well incubation plate and NADPH regeneration system were placed in a 37° C. water bath box, shaken at 100 rpm and pre-incubated for 5 min. 80 μL of incubation solution was taken out from each well of the incubation plate and added to the stop plate, mixed, and replenished with 20 μL of NADPH regeneration system solution as a 0-min sample. 80 μL of NADPH regeneration system solution was added to each well of the incubation plate to start the reaction and start counting. The corresponding compound had a reaction concentration of 1 μM and the protein concentration was 0.5 mg/mL. Separately, 100 μL of the reaction solution was taken at 10, 30, and 90 min reaction, respectively, added to a stop plate, and vortexed for 3 minutes to terminate the reaction. The stop plate was centrifuged at 5000×g at 4° C. for 4 min. 100 μL of the supernatant was added to a 96-well plate to which 100 μL of distilled water was previously added, mixed, and analyzed by LC-MS/MS.

Data analysis: The peak areas of the corresponding compound and internal standard were detected by LC-MS/MS system, and the ratio of the peak area of the compound to the internal standard was calculated. The slope was measured by plotting the natural logarithm of the percent of compound remaining versus time, and $t_{1/2}$ and $CL_{int}$ were calculated according to the formula, where V/M is equal to 1/protein concentration.

$$t_{1/2} = -\frac{0.693}{\text{slope}}, \; CL_{int} = \frac{0.693}{t_{1/2}} \cdot \frac{V}{M}; \; t_{1/2}(\text{min}), \; CL_{int}(\mu L/\text{min/mg})$$

TABLE 3

Comparison of metabolic stability of example compounds vs. Epacadostat

| Number | Human liver microsomes | | Rat liver microsomes | | Number | Human liver microsomes | | Rat liver microsomes | |
|---|---|---|---|---|---|---|---|---|---|
| | $t_{1/2}$ | $CL_{int}$ | $t_{1/2}$ | $CL_{int}$ | | $t_{1/2}$ | $CL_{int}$ | $t_{1/2}$ | $CL_{int}$ |
| Compound 11 | >150 | <9.6 | 73.3 | 18.9 | Compound 22 | >150 | <9.6 | 70.6 | 19.6 |
| Compound 32 | >150 | <9.6 | 65.0 | 21.3 | Compound 41 | >150 | <9.6 | 66.1 | 21 |

TABLE 3-continued

Comparison of metabolic stability of example compounds vs. Epacadostat

| Number | Human liver microsomes | | Rat liver microsomes | | Number | Human liver microsomes | | Rat liver microsomes | |
|---|---|---|---|---|---|---|---|---|---|
| | $t_{1/2}$ | $CL_{int}$ | $t_{1/2}$ | $CL_{int}$ | | $t_{1/2}$ | $CL_{int}$ | $t_{1/2}$ | $CL_{int}$ |
| Compound 47 | >150 | <9.6 | 74.1 | 18.7 | Compound 52 | >150 | <9.6 | 72.2 | 19.2 |
| Compound 57 | >150 | <9.6 | — | — | Compound 66 | >150 | <9.6 | 79.1 | 17.5 |
| Compound 71 | >150 | <9.6 | 67.7 | 20.5 | Compound 76 | >150 | <9.6 | 61.4 | 22.6 |
| Compound 81 | >150 | <9.6 | 75.1 | 18.5 | Epacadostat | 144 | 9.6 | 68.9 | 20.1 |

The experiment results are shown in Table 3 above. By contrast with the non-deuterated compound Epacadostat, the compounds of the present disclosure can improve the metabolic stability, and thus are more suitable for the preparation of medicaments for treating IDO-related diseases.

The above content is a further detailed description of the present disclosure in combination with specific preferred embodiments, and it cannot be assumed that the specific implementation of the present disclosure is limited to these descriptions. For a person of ordinary skill in the art to which the present disclosure belongs, a number of simple deductions or substitutions can be made without departing from the concept of the present disclosure, and should all be considered as falling within the protection scope of the present disclosure.

What is claimed is:

1. A substituted oxadiazole compound, which is a compound represented by Formula (I), or a crystal form, pharmaceutically acceptable salt, hydrate or solvate of the compound represented by Formula (I),

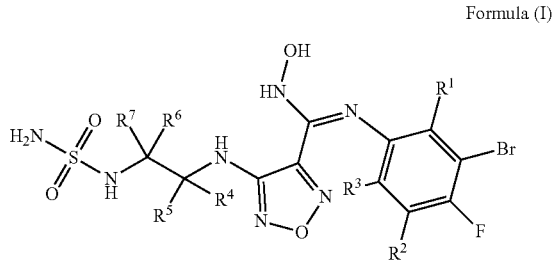

Formula (I)

wherein $R^1$, $R^2$, $R^3$, $R^4$, $R^5$, $R^6$, and $R^7$ are each independently hydrogen, deuterium, or halogen;
provided that at least one of $R^1$, $R^2$, $R^3$, $R^4$, $R^5$, $R^6$ and $R^7$ is deuterium.

2. The substituted oxadiazole compound according to claim 1, wherein $R^1$, $R^2$, and $R^3$ are each independently deuterium or hydrogen.

3. The substituted oxadiazole compound according to claim 1, wherein $R^4$ and $R^5$ are each independently deuterium or hydrogen.

4. The substituted oxadiazole compound according to claim 1, wherein $R^6$ and $R^7$ are each independently deuterium or hydrogen.

5. The substituted oxadiazole compound according to claim 1, wherein $R^4$ and $R^5$ are deuterium.

6. The substituted oxadiazole compound according to claim 1, wherein at least one of $R^1$, $R^2$, and $R^3$ is deuterium.

7. The substituted oxadiazole compound according to claim 5, wherein at least one of $R^1$, $R^2$, and $R^3$ is deuterium.

8. The substituted oxadiazole compound according to claim 1, wherein $R^6$ and $R^7$ are deuterium.

9. The substituted oxadiazole compound according to claim 5, wherein $R^6$ and $R^7$ are deuterium.

10. The substituted oxadiazole compound according to claim 6, wherein $R^6$ and $R^7$ are deuterium.

11. The substituted oxadiazole compound according to claim 7, wherein $R^6$ and $R^7$ are deuterium.

12. The substituted oxadiazole compound according to claim 1, wherein the substituted oxadiazole compound is selected from the group consisting of the following compounds or pharmaceutically acceptable salts thereof:

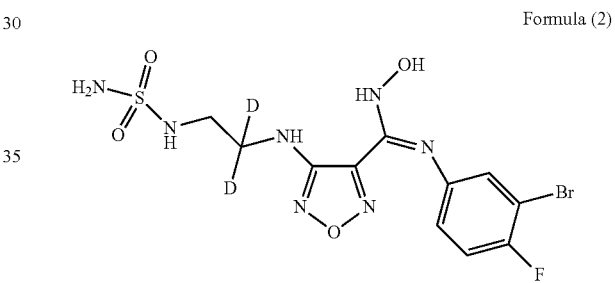

Formula (2)

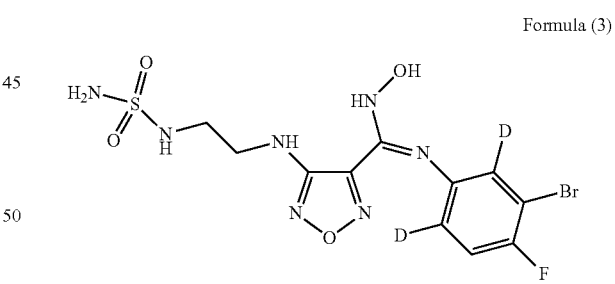

Formula (3)

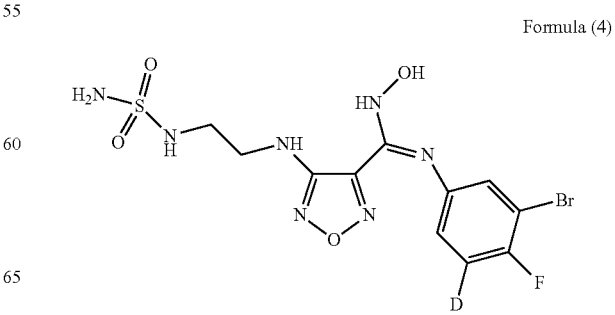

Formula (4)

Formula (5)
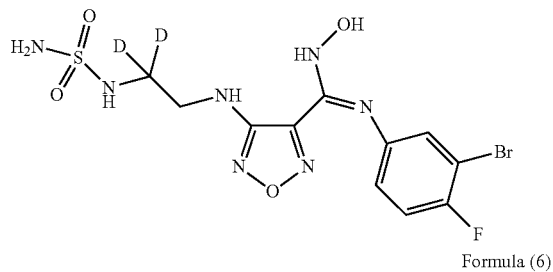
Formula (6)
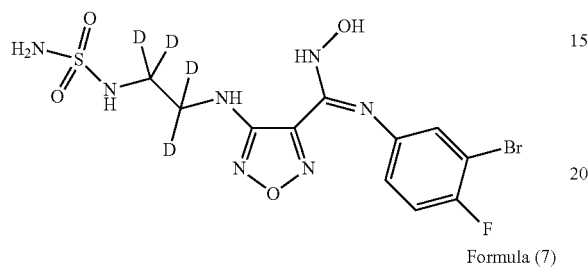
Formula (7)
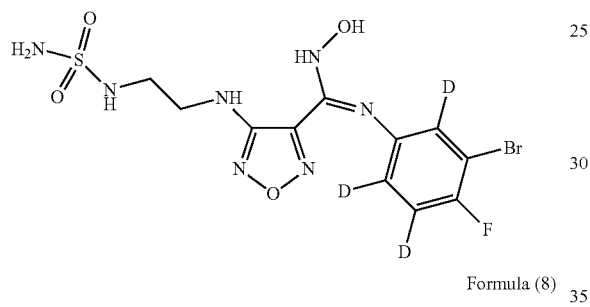
Formula (8)
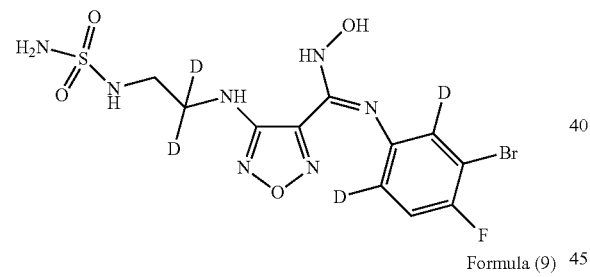
Formula (9)
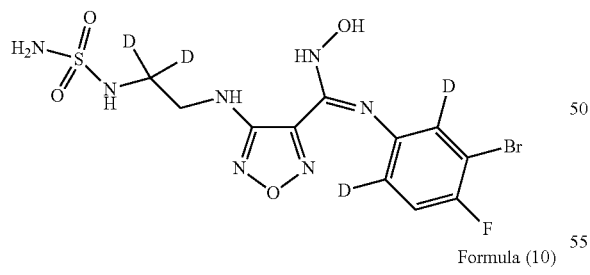
Formula (10)
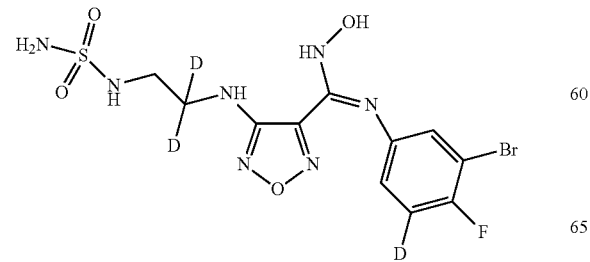
Formula (11)
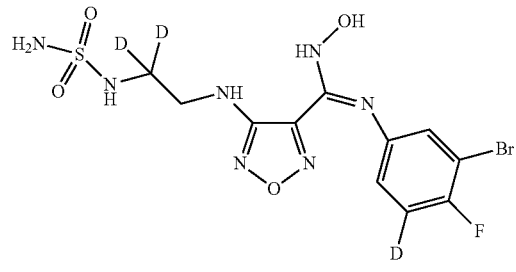
Formula (12)
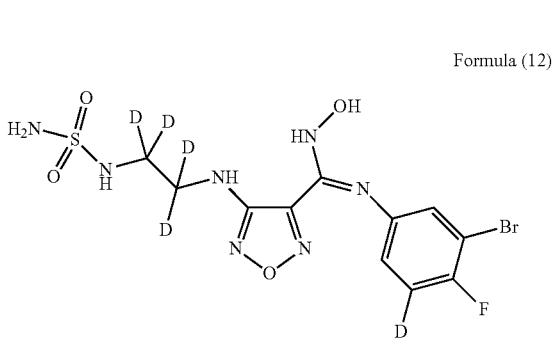
Formula (13)
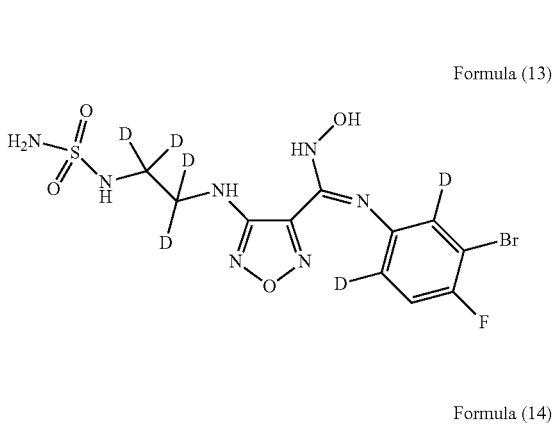
Formula (14)
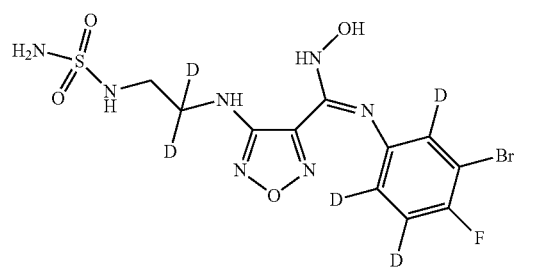
Formula (15)

Formula (16)
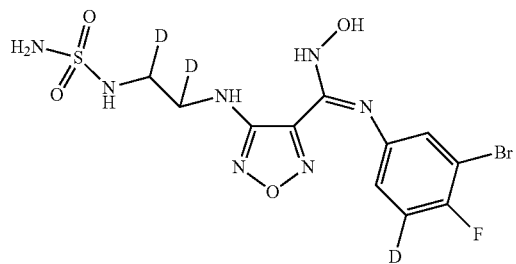

Formula (17)
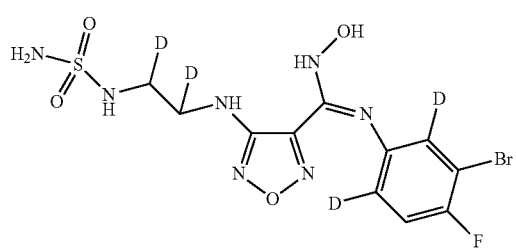

Formula (18)
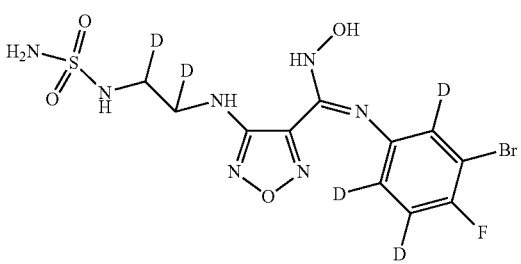

Formula (19)
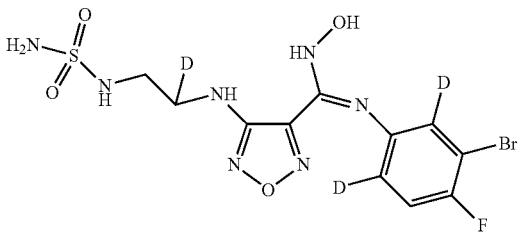

Formula (20)
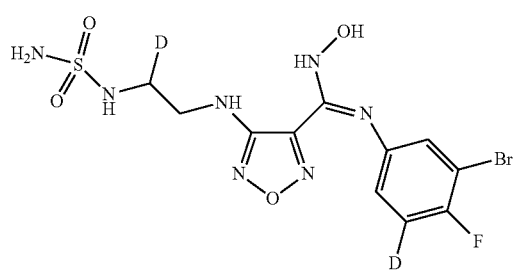

Formula (21)
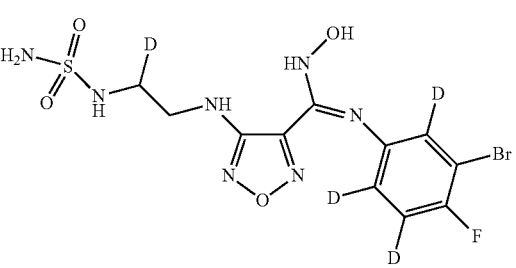

Formula (22)
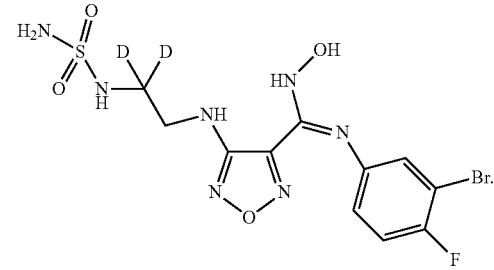 [SMILES: [2H]C([2H])(CNc1nonc1/C(=N\c1ccc(F)c(Br)c1)NO)NS(N)(=O)=O]

13. The substituted oxadiazole compound according to claim 1, which is represented by the following formula, or a crystal form, pharmaceutically acceptable salt, hydrate or solvate thereof:

14. The substituted oxadiazole compound according to claim 1, which is represented by the following formula, or a crystal form, pharmaceutically acceptable salt, hydrate or solvate thereof:

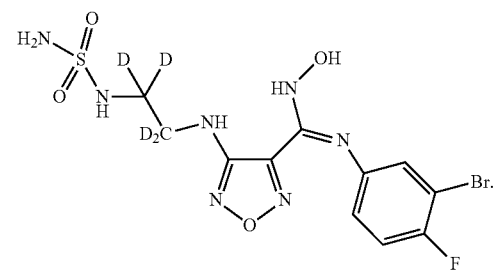

15. The substituted oxadiazole compound according to claim 1, which is represented by the following formula, or a crystal form, pharmaceutically acceptable salt, hydrate or solvate thereof:

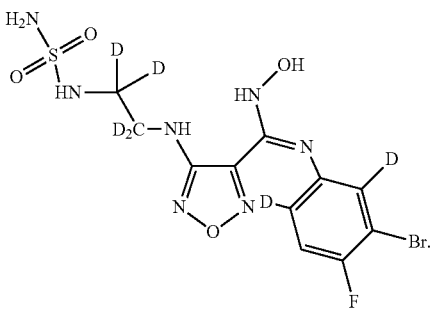

16. The substituted oxadiazole compound according to claim 1, which is represented by the following formula, or a crystal form, pharmaceutically acceptable salt, hydrate or solvate thereof:

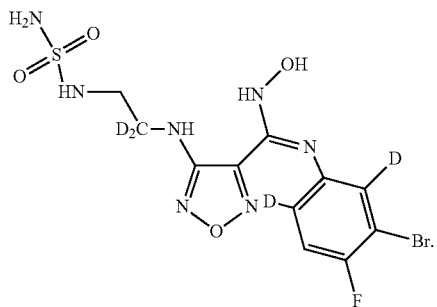

17. A pharmaceutical composition, comprising:
the substituted oxadiazole compound according to claim 1; and
a pharmaceutically acceptable carrier.

18. A method of treating and/or preventing an indoleamine 2,3-dioxygenase-mediated disease in a subject, said method comprising administering to said subject the substituted oxadiazole compound according to claim 1.

19. The method according to claim 18, wherein the indoleamine 2,3-dioxygenase-mediated disease is selected from cancer, AIDS, melanoma, neurodegenerative diseases (Alzheimer's disease, Huntington's disease and Parkinson's disease), depression, cataracts, age-related macular degeneration, and autoimmune diseases.

20. The method according to claim 18, wherein said method further comprises administering to said subject another immune checkpoint inhibitor selected from CTLA-4, PD-1, PD-L1 inhibitors.

* * * * *